(12) United States Patent
Shimizu et al.

(10) Patent No.: US 11,331,012 B2
(45) Date of Patent: May 17, 2022

(54) NON-INVASIVE BIOLIPID CONCENTRATION METER, NON-INVASIVE BIOLIPID METABOLISM MEASURING DEVICE, NON-INVASIVE METHOD FOR MEASURING BIOLIPID CONCENTRATION, AND NON-INVASIVE METHOD FOR EXAMINING BIOLIPID METABOLISM

(71) Applicant: MEDICAL PHOTONICS CO., LTD., Sapporo (JP)

(72) Inventors: Koichi Shimizu, Sapporo (JP); Kazuya Iinaga, Sapporo (JP)

(73) Assignee: MEDICAL PHOTONICS CO., LTD., Sapporo (JP)

( * ) Notice: Subject to any disclaimer, the term of this patent is extended or adjusted under 35 U.S.C. 154(b) by 564 days.

(21) Appl. No.: 16/218,966

(22) Filed: Dec. 13, 2018

(65) Prior Publication Data

US 2019/0110720 A1    Apr. 18, 2019

Related U.S. Application Data

(63) Continuation of application No. 14/649,676, filed as application No. PCT/JP2013/080826 on Nov. 14, 2013, now Pat. No. 10,188,328.

(30) Foreign Application Priority Data

Dec. 6, 2012  (JP) .................................. 2012267708

(51) Int. Cl.
*A61B 5/1455* (2006.01)
*A61B 5/00* (2006.01)
(Continued)

(52) U.S. Cl.
CPC ........ *A61B 5/1455* (2013.01); *A61B 5/14546* (2013.01); *A61B 5/4866* (2013.01);
(Continued)

(58) Field of Classification Search
None
See application file for complete search history.

(56) References Cited

U.S. PATENT DOCUMENTS 5,957,841 A     9/1999 Maruo et al.
6,493,565 B1 *  12/2002 Chance .............. A61B 5/14532
                                                 600/310
(Continued)

FOREIGN PATENT DOCUMENTS

JP     09264842 A    10/1997
JP     2002168775 A   6/2002
(Continued)

*Primary Examiner* — Marjan Fardanesh
(74) *Attorney, Agent, or Firm* — Nath, Goldberg & Meyer; Joshua B. Goldberg; Tanya E. Harkins

(57) ABSTRACT

The non-invasive biolipid concentration meter comprises: an irradiator (2) that emits light at a given intensity toward the inside of a living body from outside; a light intensity detector (3) that is disposed at a given distance from a position (21) irradiated with the light from the irradiator (2) and that determines the intensity of light emitted from the living body; a scattering coefficient calculator (4) that calculates the coefficient of light scattering within the living body on the basis of the light intensity determined with the light intensity detector (3); and a lipid concentration calculator (5) that calculates the lipid concentration in the living body on the basis of the coefficient of light scattering.

2 Claims, 13 Drawing Sheets

(51) Int. Cl.
*A61B 5/145* (2006.01)
*G01N 21/47* (2006.01)

(52) U.S. Cl.
CPC .......... *A61B 5/7225* (2013.01); *A61B 5/7278* (2013.01); *G01N 21/4795* (2013.01); *A61B 2562/0238* (2013.01)

(56) References Cited

U.S. PATENT DOCUMENTS

| | | |
|---|---|---|
| 6,615,061 B1 | 9/2003 | Khalil et al. |
| 7,551,950 B2 * | 6/2009 | Cheng .................. A61B 5/0073 600/310 |
| 2002/0082504 A1 | 6/2002 | Mizushima et al. |

FOREIGN PATENT DOCUMENTS

| | | |
|---|---|---|
| JP | 2003531357 A | 10/2003 |
| JP | 2004251673 A | 9/2004 |
| JP | 2010066280 A | 3/2010 |
| WO | 00065330 A1 | 11/2000 |

* cited by examiner

NON-INVASIVE BIOLIPID CONCENTRATION METER, NON-INVASIVE BIOLIPID METABOLISM MEASURING DEVICE, NON-INVASIVE METHOD FOR MEASURING BIOLIPID CONCENTRATION, AND NON-INVASIVE METHOD FOR EXAMINING BIOLIPID METABOLISM

This is a Continuation Application of U.S. patent application Ser. No. 14/649,676, filed Jun. 4, 2015, an application filed as a National Phase of PCT/JP2013/080826 on Nov. 14, 2013, an application claiming the benefit from Japanese Application No. 2012267708, filed Dec. 6, 2012, the contents of each of which are hereby incorporated by reference in their entirety.

TECHNICAL FIELD

The present invention relates to a non-invasive biolipid concentration measuring device, a non-invasive biolipid metabolism measuring device, a method of non-invasively measuring biolipid concentration and a method of non-invasively examining biolipid metabolism that can measure the lipid concentration and the lipid metabolism of blood in a living body in a so-called non-invasive manner without collecting blood not only in medical facilities but also at home.

BACKGROUND ART

In recent years, public healthcare expenditures are rising, and hence reduction of healthcare expenditures is the government's and public's great concern. The doctor's fees for diseases due to lifestyle related diseases account for one-third of the public healthcare expenditures. Under such circumstances, reduction of public health care expenditures, improvement of health expectancy, and improvement of QOL (Quality of Life) are demanded, and to meet such demands, specific medical examinations have been implemented, and a concept of "very early stages of disease" has been widely spread.

In particular, it is known that metabolic syndrome, which is a subject of screening in specific medical examinations, develops diabetes, dyslipidemia, high blood pressure caused by insulin resistance due to accumulation of visceral fat obesity, and it is expected that early detection of metabolic syndrome will lead to prevention of disease progression and improvement of QOL, and further, reduction of public health care expenditures.

Insulin resistance is important for early detection of lifestyle related diseases as described above; however, the only way of specific medical examinations has been measurement of abdominal girth for estimation of the risk of insulin resistance.

In recent years, a close relationship between insulin resistance and postprandial hyperlipidemia has been revealed, and a possibility that postprandial hyperlipidemia is the cause of insulin resistance has been pointed out, and therefore, postprandial hyperlipidemia can be recognized to be a metabolic error of an origin of metabolic syndrome. As such, postprandial hyperlipidemia is attracting attention not only as a factor for detecting an initial stage of metabolic syndrome (very early stages of diseases), but also as a risk factor of arteriosclerosis. For example, it can be said that when the triglyceride concentration in a non-fasting state is high, the risk of developing coronary heart disease is high.

However, diagnosis of postprandial hyperlipidemia requires observation of variation in lipid concentration in blood during 6 to 10 hours after eating. That is, to measure the state of hyperlipidemia after eating, it is required to hold examinees for about 6 to 10 hours to collect blood multiple times, but such an operation can be implemented only in clinical research and cannot be practically implemented in clinical sites.

In addition, with increasing public health consciousness, specified functional foods that inhibit fat absorption and the like are coming into practical use, and consciousness of dietary ingestion of fat is rising. Although the people are conscious to blood lipid, there is no health management apparatus for easily measuring blood lipid at home. One reason for this is that blood collection itself is restricted by the Medical Practitioners' Act, and even if there is no such restriction, examination apparatuses are not available in the price range for ordinary families. Furthermore, there are problems such as disposal of waste liquid, and long analysis time.

Under such circumstances, the following techniques relating to a blood component measurement method have been proposed.

For example, Japanese Patent Application Laid-Open No. 2004-251673 (PTL 1) discloses a technique relating to an apparatus that calculates the concentration of a measurement object by outputting and emitting light having a wavelength of a near-infrared region and an infrared region with an acoustic optical variable vibration filter to a living body, and by analyzing and computing an absorption spectrum obtained by receiving light that has transmitted through a measurement object or reflected by the measurement object. That is, the technique disclosed in PTL 1 is directed to calculate the amount of absorbed light and the like from the difference between the amount of emitted light and the amount of received light and the like by utilizing a phenomenon in which light is absorbed by blood component, to thereby calculate the blood component concentration from the results of the calculation.

In addition, Japanese Patent Application Laid-Open No. 2010-66280 (PTL 2) discloses a technique relating to a quantitative apparatus for analyzing glucose concentration including: a near-infrared light source; a detection means that detects near-infrared light; a guiding means that introduces near-infrared light emitted by the near-infrared light source to a biological tissue or bodily fluid and guides near-infrared light passing through or deffusely reflected by the biological tissue or the bodily fluid to the detection means; and a computing means that performs a regression analysis of the glucose concentration based on signals obtained by the detection means. The computing means carries out quantification using continuous spectrum signals obtained by continuously measuring wavelengths in at least three adjacent wavelength regions as defined below as explanatory variables, and the glucose concentration as a criterion variable; a first wavelength region is in a range of 1,550 to 1,650 nm to measure absorption derived from OH groups in a glucose molecule, a second wavelength region is in a range of 1,480 to 1,550 nm to measure absorption derived from NH groups in a biological component, and a third wavelength region is in a range of 1,650 to 1,880 nm to measure absorption derived from CH groups in the biological component, within the wavelength region from 1,480 to 1,880 nm in which harmonics of a first harmonic tone is observed, and in which the effect of water absorption is relatively small. That is, as with the technique disclosed in PTL 1, the technique disclosed in PTL 2 utilizes a phenomenon in which light is absorbed by the NH group, CH group and OH group of glucose to calculate the amount of absorbed light from the difference between the amount of emitted light and the amount of received light and the like, to thereby calculate the concentration of the blood component from the results of the calculation.

Further, Japanese Patent Application Laid-Open No. 2002-168775 (PTL 3) discloses a technique relating to a rapid measuring method of a plasma component of a mammal by spectrum information in a visual and near-infrared region, which is characterized by measuring an absorbance in the visual and near-infrared region having a wavelength of 400-2,500 nm by using a near-infrared spectrophotometer relative to separated plasma in measuring the plasma component of the mammal, calculating a primary differential and a secondary differential of the absorbance, using the absorbance, and the primary differential and the secondary differential of the absorbance in the visual and near-infrared region as independent variables, selecting independent variables to the number of two to ten having high explanation power from among the independent variables, predicting triglyceride, inorganic phosphorus, potassium, lactate dehydrogenase and an albumin-globulin ratio in the plasma from the information on the independent variables having high explanation power, and realizing measurement based on the predicted values. That is, as with the techniques of PTL 1 and PTL 2, the technique of PTL 3 utilizes a phenomenon in which plasma absorbs visible light having wavelengths of 400-2500 nm and light of a near-infrared region to calculate the triglyceride concentration and the like in plasma from the difference between the amount of emitted light and the amount of received light and the like.

CITATION LIST

Patent Literatures

PTL 1
Japanese Patent Application Laid-Open No. 2004-251673
PTL 2
Japanese Patent Application Laid-Open No. 2010-66280
PTL 3
Japanese Patent Application Laid-Open No. 2002-168775

SUMMARY OF INVENTION

Technical Problem

However, while the techniques disclosed in PTLS 1 to 3 are based on a phenomenon in which light is absorbed by a certain blood component and require elimination of scattering of light, the researches so far show that the influence of absorption is about 1/10 of the influence of scattering, that is, the influence of scattering is about 10 times the influence of absorption, and therefore it is very difficult to eliminate the influence of scattering. In addition, while it is not necessary to eliminate the influence of scattering when the scattering is constant, it is difficult to determine whether the actually measured light intensity has been influenced by absorption or scattering, and the length of the light path also has an influence, thus making it difficult to achieve measurement. In particular, in the case of non-invasive measurement, the influence of absorption by other substances such as cells has to be taken into consideration, and therefore it is practically impossible to achieve non-invasive measurement using the techniques disclosed in PTLS 1 to 3. In addition, the apparatus based on PTLS 1 to 3 has a large size, and is expensive, and therefore, such an apparatus cannot be practically easily used at home. Further, when the distance between the irradiation position and the detection position is increased, the length of the light path is increased, and consequently the light energy may possibly be completely absorbed without being output to the outside in absorption measurement.

In addition, in the technique disclosed in PTL 1, the wavelength range within which light is easily absorbed by lipid, sugar and the like, and the wavelength range within which light is easily absorbed by water and electrolyte of blood overlap each other, and when light of the overlapped wavelength range is used, the influence of light absorption by lipid, sugar and the like is hidden by the influence of light absorption by water and electrolyte, and consequently the amount of light absorbed by lipid, sugar and the like may not possibly be correctly measured.

Further, in the technique disclosed in PTL 2, the glucose concentration in blood is quantified based on a phenomenon in which emitted light is absorbed by a hydrophilic group such as OH group, NH group and CH group of glucose, and therefore the measurement object is disadvantageously limited. In other words, the blood lipid concentration cannot be measured. To be more specific, blood lipid has high hydrophobicity, and has a spherical structure covered by phospholipid and the like. One reason for this is that cholesterol ester and triglyceride in blood have hydrophobicity and poor affinity to water, and exhibit poor solubility to water, thus presenting as scattering members forming micelle covered with amphiphilic phospholipid. In addition, while the triglyceride measured in common medical examinations and diagnoses of disease is triglyceride and the total cholesterol is the sum of cholesterol, cholesterol ester, free cholesterol and the like, it is said that cholesterol ester is important in terms of the risk of arteriosclerosis. As described, since the lipid component that is an important measurement object presents in the center of micelle because of its high hydrophobicity, and the micelle surface has a light reflecting property, it is difficult to measure the concentration of the substance based on absorption. In addition, in the technique disclosed in PTL 2, the concentration is calculated by regression analysis of obtained light absorbance, and therefore cannot be measured in real time.

Furthermore, in the technique disclosed in PTL 3, the measurement object is obtained by collecting blood and then separating plasma from blood, and therefore, the technique disclosed in PTL 3 is not directed to a non-invasive measurement. That is, a triglyceride concentration and the like can be detected only when disturbances such as a living body and other blood components are removed, that is, when a state where the influence of scattering is removed is established. As such, unlike the present invention, in PTL 3 contains no solution for difficulty in non-invasive detection of the triglyceride concentration in blood.

In addition, while a dynamic light scattering method and a static light scattering method are available as techniques for measuring a blood component based on light scattering, the methods are directed to measure the size of blood component, not to calculate concentration. In addition, the dynamic light scattering method is a method for measuring Brownian motion to calculate particle diameter distribution, and the measurement object is required to be statically placed, and therefore it is difficult to measure a dynamic object such as blood flow. Required measurement time is about 30 minutes to one hour per sample. Meanwhile, the static light scattering method is a method for calculating the molecular weight in the case where the component is a single component and the concentration is determined, and the static light scattering method is intended for measurement of particles having a size greater than that can be measured by the dynamic light scattering method, and movement of molecules during analysis is not assumed. Therefore, also in the static light scattering method, the measurement object is required to be statically placed, and therefore it is difficult to measure a dynamic object such as blood flow.

To solve the above-mentioned problems, an object of the present invention is to provide a non-invasive biolipid concentration measuring device, a non-invasive biolipid metabolism measuring device, a method of non-invasively measuring biolipid concentration and a method of non-invasively examining biolipid metabolism which do not require blood collection and allow measurement of blood lipid not only in medical facilities but also at home, and moreover, which achieves instant data acquisition and time-series measurement of blood lipid and can be applied to examination of metabolic errors such as postprandial hyperlipidemia.

Solution to Problem

A non-invasive biolipid concentration measuring device according to an embodiment of the present invention is configured to non-invasively measure a blood lipid concentration in a living body, the non-invasive biolipid concentration measuring device including:

an irradiator configured to emit light having a given light intensity toward an inside of the living body from an outside;

a light intensity detector disposed at a position separated by a given distance from an irradiation position to which light is emitted by the irradiator, the light intensity detector being configured to detect a light intensity of light emitted from the living body;

a scattering coefficient calculator configured to calculate a light scattering coefficient in the living body based on the light intensity detected by the light intensity detector; and a lipid concentration calculator configured to calculate a lipid concentration in the living body based on the light scattering coefficient calculated by the scattering coefficient calculator.

Preferably, in the non-invasive biolipid concentration measuring device and the method of non-invasively measuring a biolipid concentration according to the embodiment of the present invention, the irradiation position and a detection position at which the light intensity is detected are separated by a given irradiation-detection distance, and a light intensity of light emitted by rearward scattering light scattered by blood lipid in the living body is detected by the light intensity detector detects, or determined by the detection.

Preferably, in the non-invasive biolipid concentration measuring device and the method of non-invasively measuring a biolipid concentration according to the embodiment of the present invention, the irradiation position and a detection position at which the light intensity is detected are separated by a given irradiation-detection distance, and the light intensity detector detects a light intensity of light emitted by rearward scattering light scattered by blood lipid in the living body, or a light intensity of light emitted by rearward scattering light scattered by blood lipid in the living body is determined by the detection.

Preferably, in the non-invasive biolipid concentration measuring device and the method of non-invasively measuring a biolipid concentration according to the embodiment of the present invention, the scattering coefficient calculator calculates a light scattering coefficient in the living body based on a ratio of a detected light intensity to an irradiation-detection distance between the irradiation position and a detection position at which the light intensity is detected, or a light scattering coefficient in the living body is determined by the calculation based on a ratio of a detected light intensity to an irradiation-detection distance between the irradiation position and a detection position at which the light intensity is detected.

Preferably, in the non-invasive biolipid concentration measuring device and the method of non-invasively measuring a biolipid concentration according to the embodiment of the present invention, the scattering coefficient calculator calculates a light scattering coefficient in the living body based on a ratio of a detected light intensity to an irradiation-detection distance between the irradiation position and a detection position at which the light intensity is detected, or a light scattering coefficient in the living body is determined by the calculation based on a ratio of a detected light intensity to an irradiation-detection distance between the irradiation position and a detection position at which the light intensity is detected.

Preferably, in the non-invasive biolipid concentration measuring device and the method of non-invasively measuring a biolipid concentration according to the embodiment of the present invention, the irradiator emits consecutive light, or consecutive light is emitted toward the inside of the living body from the outside during the emission, or consecutive light is emitted toward the inside of the living body from the outside during the emission; and the scattering coefficient calculator calculates scattering coefficient $\mu_s'$ by applying light intensity $R(\rho)$ detected by the light intensity detector and the irradiation-detection distance $\rho$ into Expression (1) and Expression (2), or scattering coefficient $\mu_s'$ is determined by the calculation by applying light intensity $R(\rho)$ determined by the detection and the irradiation-detection distance $\rho$ into Expression (1) and Expression (2)

$$\ln\left\{\rho^2 \frac{R(\rho)}{S_0}\right\} = -\mu_{eff}\rho + \ln\frac{3\mu_a}{2\pi\mu_{eff}} \qquad \text{[Expression 1]}$$

$$\ln\left\{\rho^3 \frac{R(\rho)}{S_0}\right\} = -\mu_{eff}\rho + \ln\frac{1}{2\pi\mu_s'} \qquad \text{[Expression 2]}$$

where $\mu_a$ represents an absorption coefficient, $\mu_{eff}$ an effective attenuation coefficient, and $S_0$ a light intensity of light emitted by the irradiator.

Preferably, in the non-invasive biolipid concentration measuring device and the method of non-invasively measuring a biolipid concentration according to the embodiment of the present invention, the irradiator emits consecutive light, or consecutive light is emitted toward the inside of the living body from the outside during the emission;

light intensities at respective detection positions of a plurality of the light intensity detectors are detected by the light intensity detectors, the light intensity detectors being disposed around an irradiation position at respective positions separated by respective different distances from the irradiation position, the irradiation position being a position to which consecutive light is emitted by the irradiator, or light intensities at respective detection positions are detected, the detection positions being disposed around an irradiation position at respective positions separated by respective different distances from the irradiation position, the irradiation position being a position to which consecutive light is emitted during the emission; and the scattering coefficient calculator calculates a light scattering coefficient in the living body based on a ratio and/or a difference of light intensities detected by the light intensity detectors, or a light scattering coefficient in the living body is determined by the calculation based on a ratio and/or a difference of the light intensities determined by the detection.

Preferably, in the non-invasive biolipid concentration measuring device and the method of non-invasively measuring a biolipid concentration according to the embodiment of the present invention, the irradiator emits consecutive light, or consecutive light is emitted toward the inside of the living body from the outside during the emission;

a first light intensity detector and a second light intensity detector are arranged in order around an irradiation position at respective positions separated from the irradiation position by respective different distances, the irradiation position being a position to which consecutive light is emitted by the irradiator, or the light intensity is detected at a first detection position and a second detection position disposed around an irradiation position at respective positions separated from the irradiation position by respective different distances, the irradiation position being a position to which consecutive light is emitted during the emission; and the scattering coefficient calculator calculates scattering coefficient $\mu_s'$ by applying into Expression (3) first irradiation-detection distance $\rho_1$ between the irradiation position and a first detection position of the first light intensity detector, second irradiation-detection distance $\rho_2$ between the irradiation position and a second detection position of the second light intensity detector, first light intensity R ($\rho_1$) detected by the first light intensity detector, and second light intensity R ($\rho_2$) detected by the second light intensity detector, or scattering coefficient $\mu_s'$ is determined by the calculation by applying into Expression (3) first irradiation-detection distance $\rho_1$ between the irradiation position and the first detection position, second irradiation-detection distance $\rho_2$ between the irradiation position and the second detection position, first light intensity R ($\rho_1$) detected at the first detection position, and second light intensity R ($\rho_2$) detected at the second detection position.

$$\mu_s' = \frac{1}{3\mu_a}\left\{\frac{1}{\rho_2-\rho_1}\ln\frac{\rho_1^2 R(\rho_1)}{\rho_2^2 R(\rho_2)}\right\}^2 \qquad \text{[Expression 3]}$$

Preferably, in the non-invasive biolipid concentration measuring device and the method of non-invasively measuring a biolipid concentration according to the embodiment of the present invention, the irradiator emits pulsed light, or pulsed light is emitted toward the inside of the living body from the outside during the emission;

the light intensity detector detects the light intensity at specified time intervals, or the light intensities at specified time intervals are determined by the detection; and the scattering coefficient calculator calculates a light scattering coefficient in the living body based on a length of a period until the light intensity detected by the light intensity detector is attenuated to a given intensity after pulsed light is emitted by the irradiator, or a light scattering coefficient in the living body is determined by the calculation based on a length of a period until the light intensity determined by the detection is attenuated to a given intensity after pulsed light is emitted.

Preferably, in the non-invasive biolipid concentration measuring device and the method of non-invasively measuring a biolipid concentration according to the embodiment of the present invention, the irradiator emits pulsed light, or pulsed light is emitted toward the inside of the living body from the outside during the emission;

the light intensity detector detects the light intensity at specified time intervals, or the light intensities at specified time intervals are determined by the detection; and the scattering coefficient calculator calculates a light scattering coefficient in the living body based on a length of a period until the light intensity detected by the light intensity detector reaches a highest value after pulsed light is emitted by the irradiator, or a light scattering coefficient in the living body is determined by the calculation based on a length of a period until the light intensity determined by the detection reaches a highest value after pulsed light is emitted.

Preferably, in the non-invasive biolipid concentration measuring device and the method of non-invasively measuring a biolipid concentration according to the embodiment of the present invention, light obtained by modulating an intensity or a phase of light emitted by the irradiator is emitted, or light obtained by modulating an intensity or a phase of light emitted during the emission is emitted;

the light intensity detector detects the light intensity at specified time intervals, or the light intensities at specified time intervals are determined by the detection; and the scattering coefficient calculator calculates a light density waveform based on a time variation of the light intensity detected by the light intensity detector, and calculates a scattering coefficient and an absorption coefficient of the blood based on the light density waveform, or, during the calculation, a light density waveform is determined based on a time variation of the light intensity determined by the detection, and a scattering coefficient and an absorption coefficient of the blood are determined based on the light density waveform.

A non-invasive biolipid metabolism measuring device according to the embodiment of the present invention is configured to measure biolipid metabolism from a time variation of a scattering coefficient and/or a lipid concentration calculated by the non-invasive biolipid concentration measuring device.

A method of non-invasively examining biolipid metabolism according to the embodiment of the present invention includes: acquiring a time variation of a scattering coefficient and/or a lipid concentration calculated by the non-invasive biolipid concentration measuring device to examine biolipid metabolism.

Advantageous Effects of Invention

According to the present invention, since blood collection is not required, blood lipid can be measured not only in medical facilities but also at home, and moreover, since instant data acquisition is achieved and blood lipid can be measured in a temporally continuous manner, the present invention can be applied to examination of metabolic errors such as postprandial hyperlipidemia.

DESCRIPTION OF EMBODIMENTS

In the following, a non-invasive biolipid concentration measuring device, a non-invasive biolipid metabolism measuring device, a method of non-invasively measuring biolipid concentration and a method of non-invasively examining biolipid metabolism according to an embodiment of the present invention are described with reference to the drawings.

Figure 1:
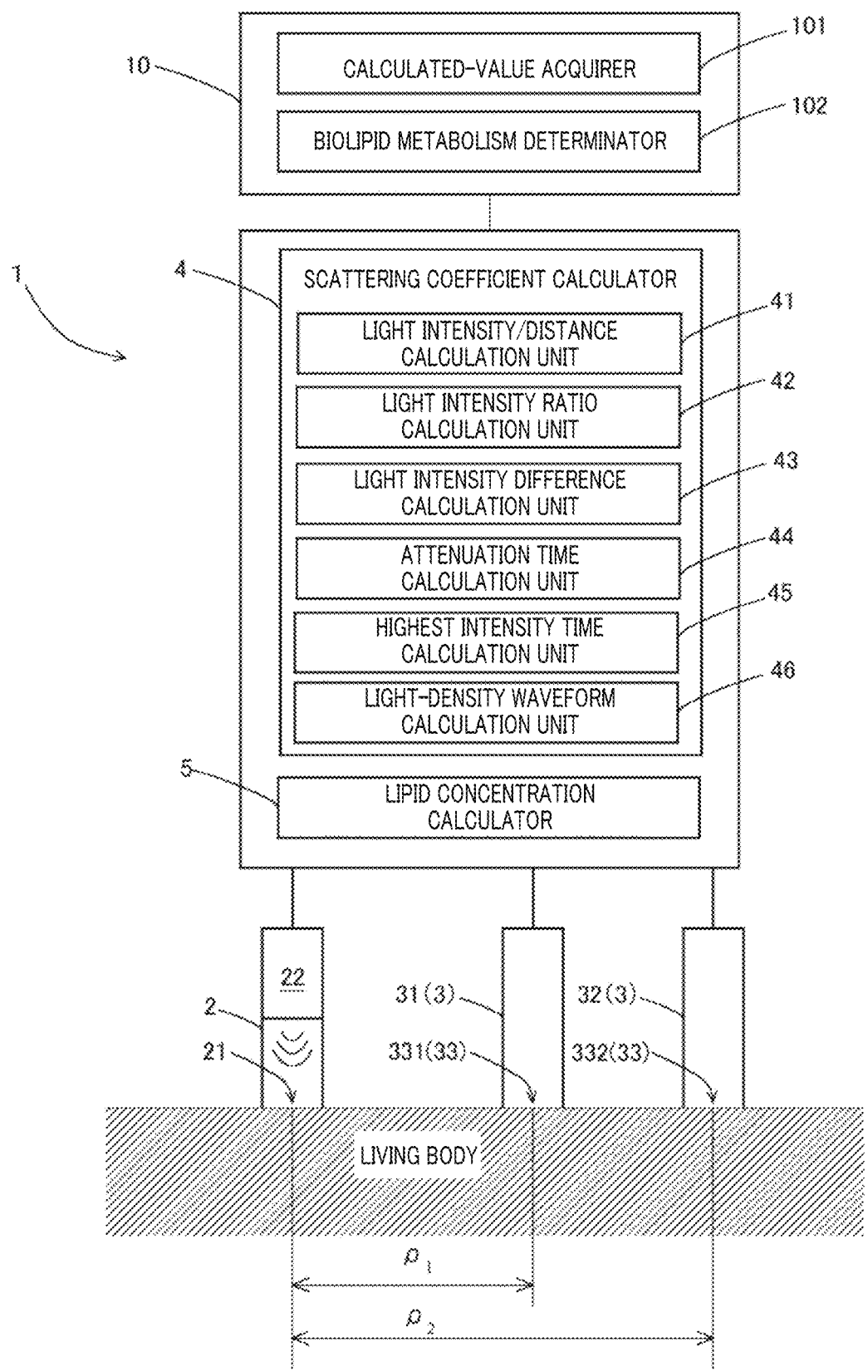
FIG. 1 illustrates a non-invasive biolipid concentration measuring device and a non-invasive biolipid metabolism measuring device according to an embodiment of the present invention.

As illustrated in FIG. 1, non-invasive biolipid concentration measuring device 1 of the present embodiment includes: irradiator 2 that emits light toward a living body from outside; light intensity detector 3 that detects a light intensity at a given detection position 31 outside the living body; scattering coefficient calculator 4 that calculates light scattering coefficient $\mu_s'$ in the living body based on the light intensity detected by the light intensity detector; and lipid concentration calculator 5 that calculates the lipid concentration in the living body based on light scattering coefficient $\mu_s'$ calculated with scattering coefficient calculator 4. That is, non-invasive biolipid concentration measuring device 1 of the present embodiment performs quantitative analysis of blood lipid with use of light which easily transmits through a living body so as to achieve examination without blood collection.

In the following, the components are described in detail.

As illustrated in FIG. 1, irradiator 2 emits light toward a living body from outside to irradiate given irradiation position 21 with the light, and has light source 22 for emitting light. In light source 22, the wavelength of light to be emitted can be freely adjusted, and the wavelength can be adjusted to a wavelength falling outside the wavelength range within which the light is absorbed by inorganic substances of plasma. In addition, in light source 22 of the present embodiment, the wavelength of light to be emitted can be adjusted to a wavelength falling outside the wavelength range within which the light is absorbed by cell components of blood. Here, the cell components of blood include red blood cells, white blood cells and platelets in blood, and the inorganic substances of plasma include water and electrolyte in blood.

Figure 2:
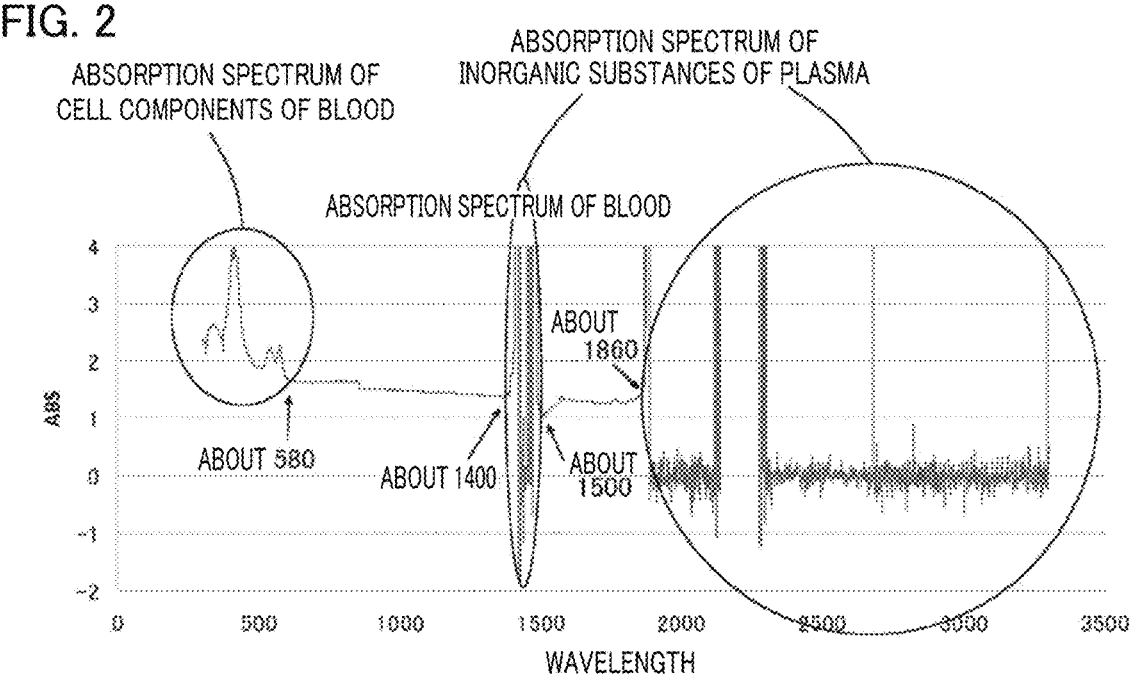
FIG. 2 illustrates a light absorption spectrum of blood.

In addition, the wavelength range within which light is absorbed by inorganic substances of plasma is, mainly, a range within which light absorption by inorganic substances of plasma is significant, and is a range as shown in FIG. 2. Likewise, the wavelength range within which light is absorbed by cell components of blood is, mainly, a range within which light absorption by cell components of blood is significant, and is a range as shown in FIG. 2. While it can be said that light that falls outside the above-mentioned wavelength ranges is absorbed by inorganic substances of plasma and by cell components of blood, such absorption is negligible in experiment and biological measurement.

That is, as shown in FIG. 2, the wavelength range of light source 22 is preferably set to about 1400 nm or smaller, and about 1500 nm to about 1860 nm in consideration of the wavelength range within which light is absorbed by inorganic substances of plasma, more preferably, about 580 nm to about 1400 nm, and about 1500 nm to about 1860 nm in consideration of the wavelength range within which light is absorbed by cell components of blood.

In this manner, by setting the wavelength range of light source 22 to the above-mentioned range, the influence of light absorption by inorganic substances of plasma and the influence of light absorption by cell components of blood are limited in light detected by light intensity detector 3 described later. With this configuration, absorption that specifies substances does not occur and the loss of light energy due to absorption is negligibly small, and thus light in blood is propagated to a distant position by scattering by blood lipid and emitted to the outside of the body.

In addition, in irradiator 2 of the present embodiment, in accordance with the method of calculating scattering coefficient $\mu_s'$ of scattering coefficient calculator 4 described later, the time length of consecutive light emission, pulsed light emission and the like can be arbitrarily adjusted, and the intensity or phase of light to be emitted can be arbitrarily modulated.

Alternatively, in irradiator 2, light source 22 that uses fixed wavelength, or light source 22 that uses multiple wavelengths together may be adopted.

Light intensity detector 3 is configured to receive light to detect the intensity of the light. Light intensity detector 3 can receive light emitted to the outside from a living body, and detect the intensity of the light. In addition, in the case where a plurality of light intensity detectors 3 are employed, light intensity detectors 3 are disposed around irradiation position 21 with different distances therebetween. In the present embodiment, as illustrated in FIG. 1, first light intensity detector 31 and second light intensity detector 32 are linearly arranged on the same plane with given distances from irradiation position 21 therebetween.

In addition, the distance from irradiation position 21 to detection position 33 is defined as irradiation-detection distance ρ. In the present embodiment, as illustrated in FIG. 1, the distance from irradiation position 21 to first detection position 331 of first light intensity detector 31 is defined as first irradiation-detection distance $\rho_1$, and the distance from irradiation position 21 to second detection position 332 of second light intensity detector 32 is defined as second irradiation-detection distance $\rho_2$.

Figure 3:
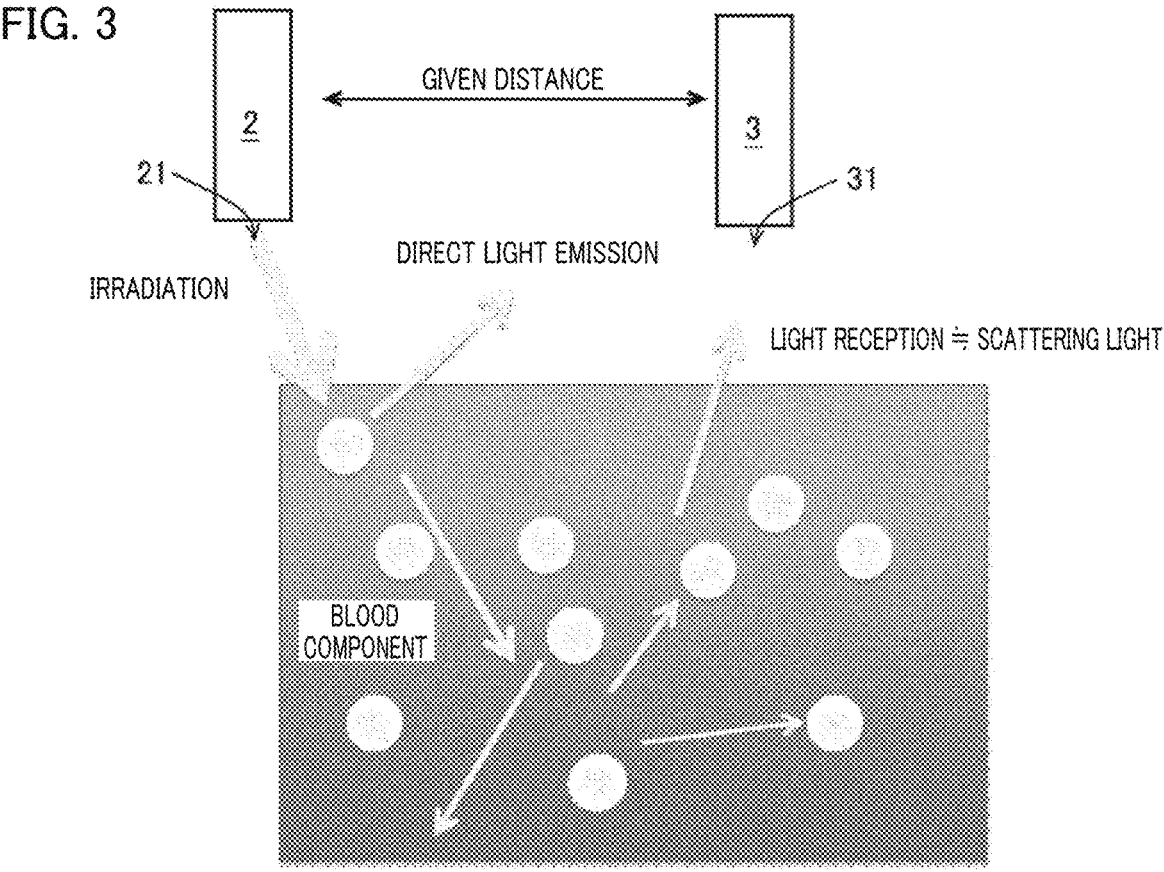
FIG. 3 is a schematic view illustrating light detected in the present embodiment which contains information of scattering of light by blood lipid.

As illustrated in FIG. 3, by providing a given distance between irradiation position 21 at which a living body is irradiated with light and detection position 33 at which the intensity of light emitted from the living body is detected as described above, the influence of emission light, which is reflected by scattering members near the biological surface or on the biological surface and is directly emitted from the living body, is limited, and the light intensity of rearward scattering light, which is emitted from the living body after reaching the depth where blood and lipid present and after being scattered by reflection by blood lipid, is detected. In addition, by increasing the distance between irradiation position 21 and detection position 33, the length of the light path is increased and the frequency of collision with lipid is increased. As a result, the detected light is more influenced by the light scattering. Thus, the influence of scattering, which is conventionally weak and cannot be easily detected, is easily detected.

Figure 4:
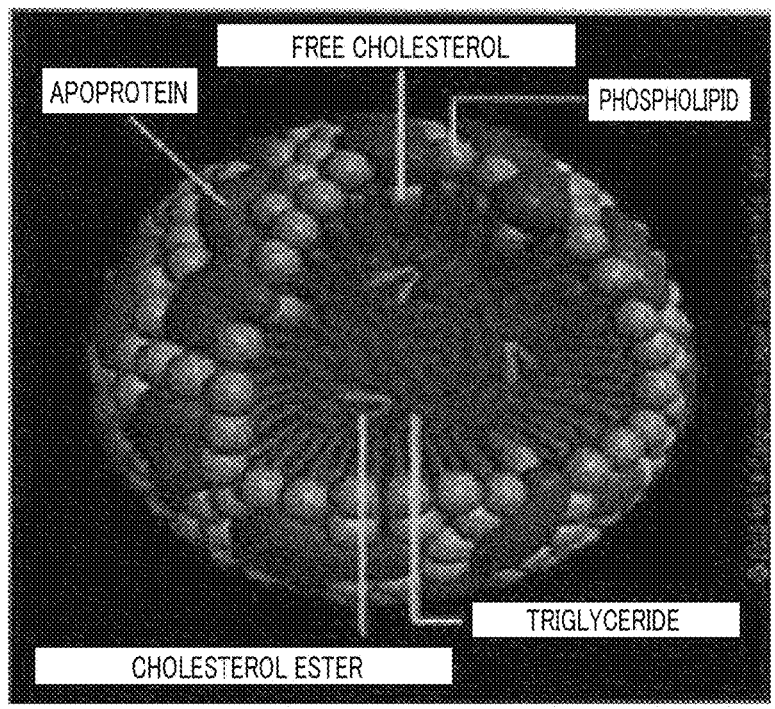
FIG. 4 is a schematic view illustrating a structure of lipoprotein.

In addition, "blood lipid," which is a measurement object, has a spherical structure covered with apoprotein or the like as illustrated in FIG. 4, and is called lipoprotein. In addition, lipid itself is a hydrophobic substance and is nearly insoluble in blood. Therefore, blood lipid in blood is in a solid-like state, and has a light reflectivity. In particular, chylomicron (CM), VLDL and the like, which have a large particle size and specific gravity, contain a large amount of lipid and tend to easily cause light scattering. Accordingly, it can be said that the light intensity detected by light intensity detector 3 is influenced by light scattering of blood lipid.

It is to be noted that in the case where a plurality of detection positions 33 are provided, the layout of detection positions 33 is not limited to the linear form as long as detection positions 33 are disposed around irradiation position 21 with different distances therebetween, and the layout may be appropriately selected from various forms such as a circular form, a wave form, and a zigzag form. In addition, first irradiation-detection distance $\rho_1$ and second irradiation-detection distance $\rho_2$ between irradiation position 21 and detection position 33, and the distance between detection positions 331 and 332 are not limited to constant distances, and may be appropriately selected.

Scattering coefficient calculator 4 is configured to calculate light scattering coefficient $\mu_s'$ in a living body based on the light intensity detected by light intensity detector 3. The light intensity detected by light intensity detector 3 is influenced by light scattering of blood lipid as described above, and this feature is utilized to calculate scattering coefficient $\mu_s'$. It is to be noted that scattering coefficient $\mu_s'$ in the present embodiment is not limited to a coefficient obtained by digitizing the efficiency of a typical scattering process, and scattering coefficient $\mu_s'$ in the present embodiment includes a coefficient obtained by digitizing the influence of scattering under a constant condition in consideration of a scattering phenomenon. Details are described below.

As illustrated in FIG. 1, scattering coefficient calculator 4 in the present embodiment includes six calculation units, specifically, light intensity/distance calculation unit 41, light intensity ratio calculation unit 42, light intensity difference calculation unit 43, attenuation time calculation unit 44, highest intensity time calculation unit 45 and light-density waveform calculation unit 46. In the following, the calculation units are described in detail.

Figure 5:
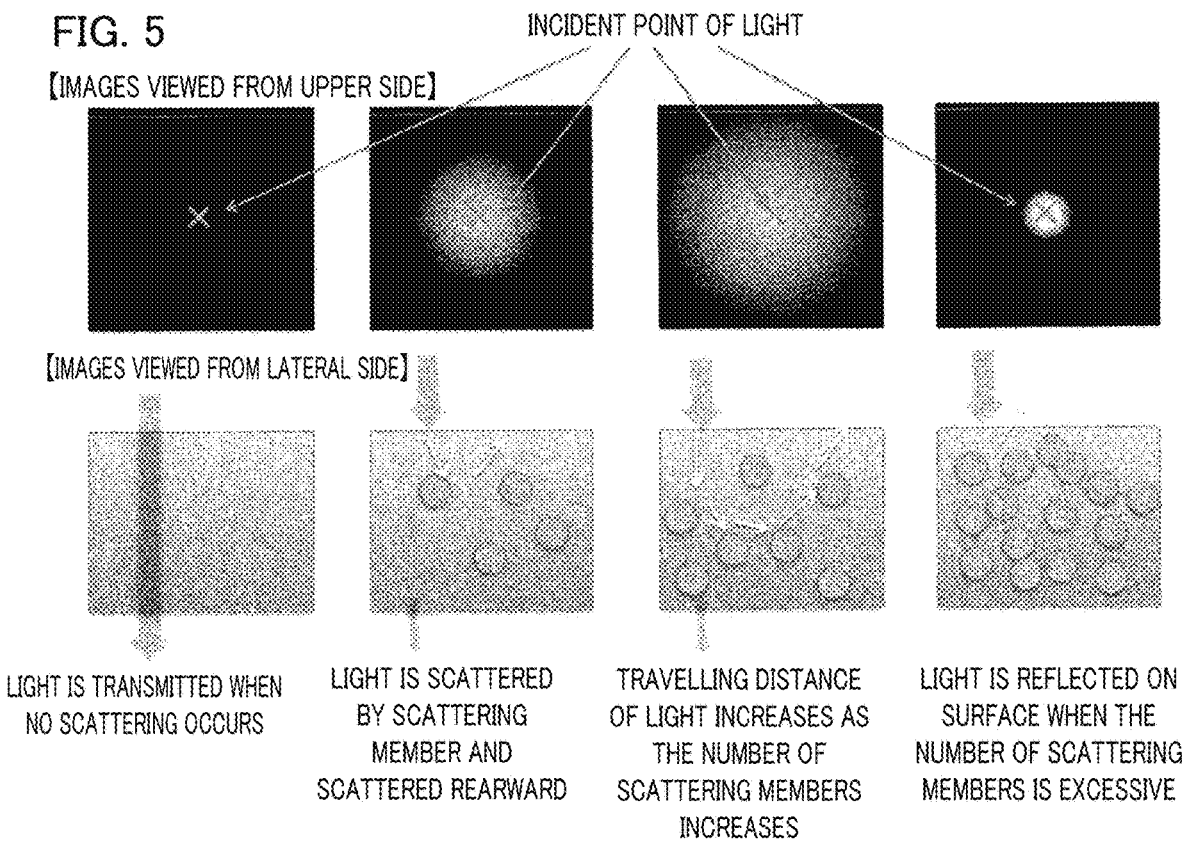
FIG. 5 is images viewed from the upper side and images viewed from a lateral side that show influences of light scattering corresponding to the concentration of particles when blood is irradiated with light.

Light intensity/distance calculation unit 41 is configured to calculate scattering coefficient $\mu_s'$ based on a ratio of the light intensity detected at detection position 33 to irradiation-detection distance $\rho$ between irradiation position 21 and detection position 33. That is, scattering coefficient $\mu_s'$ is calculated based on a scattering phenomenon in which emitted light is attenuated by scattering as the distance to the detection position is increased. That is, as illustrated in FIG. 5, emitted light is transmitted through blood and no scattering is caused when there is no particle that cause scattering in blood (the first image from left). When blood contains scattering particles and scattering is caused, emitted light is reflected and emitted from the living body. Here, distributions differ depending on the concentration of the particles. Specifically, weak light may reach a position close to irradiation position 21 (the second image from left), light may reach a position distant from irradiation position 21 (the third image from left), or strong light may reach a position close to irradiation position 21 (the fourth image from left).

Therefore, the light intensity detected here contains, as described above, information of light scattering corresponding to the concentration of lipid in a particle form in blood, and information of attenuation of light intensity that is facilitated as the distance between irradiation position 21 and detection position 33 increases. Therefore, light intensity/distance calculation unit 41 calculates the ratio of the light intensity to the distance between irradiation position 21 and detection position 33 which is determined by the setting, that is, a so-called attenuation rate to the distance, and light intensity/distance calculation unit 41 uses the calculated value as scattering coefficient $\mu_s'$, thus obtaining scattering coefficient $\mu_s'$ dependent on the blood lipid concentration.

Light intensity/distance calculation unit 41 in the present embodiment emits consecutive light from irradiator 2, and applies light intensity R ($\rho$) detected by first light intensity detector 31 and irradiation-detection distance $\rho_1$ into the following Expression (1) and Expression (2) to calculate scattering coefficient $\mu_s'$ $$\ln\left\{\rho^2 \frac{R(\rho)}{S_0}\right\} = -\mu_{eff}\rho + \ln\frac{3\mu_a}{2\pi\mu_{eff}} \quad \text{[Expression 1]}$$

$$\ln\left\{\rho^3 \frac{R(\rho)}{S_0}\right\} = -\mu_{eff}\rho + \ln\frac{1}{2\pi\mu_s'} \quad \text{[Expression 2]}$$

where $\mu_a$ is the absorption coefficient, $\mu_{eff}$ is the effective attenuation coefficient, and $S_0$ is the intensity of the light emitted by irradiator 2.

It is to be noted that Expression (1) and Expression (2) are derived as follows.

First, as illustrated in FIG. 1, when light having a given light intensity $S_0$ is emitted as consecutive light toward the inside of a living body from outside, and when the distance from irradiation position 21 to detection position 33 is represented by irradiation-detection distance $\rho$, the distribution of the light emitted to the outside of the living body by the rearward scattering light is expressed by the following Expression (4).

$$R(\rho) = S_0 \frac{z_0}{2\pi}\left(\mu_{eff} + \frac{1}{\sqrt{\rho^2 + z_0^2}}\right)\frac{\exp\left(-\mu_{eff}\sqrt{\rho^2 + z_0^2}\right)}{\rho^2 + z_0^2} \quad \text{[Expression 4]}$$

Where $z_0$ represents the depth of the light source, that is, the depth from which scattering starts, and is expressed by the following Expression (5).

$$z_0 = \frac{1}{\mu_s'} \quad \text{[Expression 5]}$$

Where $\mu_s'$ represents the scattering coefficient.

In addition, $\mu_{eff}$ represents the effective attenuation coefficient and is expressed by the following Expression (6).

$$\mu_{eff} = \sqrt{\frac{\mu_a}{D}} = \sqrt{3\mu_a(\mu_s' + \mu_a)} \quad \text{[Expression 6]}$$

Where D and $\mu_a$ represent the diffusion coefficient and the absorption coefficient, respectively.

In addition, when scattering in a blood vessel near the skin surface or on the skin surface is assumed, the relationship between irradiation-detection distance $\rho$ and depth $z_0$ of the light source can be approximated as the following Expression (7).

$$\rho^2 + z_0^2 \approx \rho^2 \quad \text{[Expression 7]}$$

where $$\rho^2 \gg z_0^2 \left(= \frac{1}{\mu_s'^2}\right)$$

Further, as described above, the measurement object of the present embodiment of the present invention is blood lipid, and scattering by blood lipid is considered to be greater than absorption. Therefore, effective attenuation coefficient $\mu_{eff}$ can be approximated as the following Expression (8).

$$\mu_{eff} \approx \sqrt{3\mu_a\mu_s'} \quad \text{[Expression 8]}$$

where $$\mu_s' \gg \mu_a$$

When Expression (7) and Expression (8) are applied into Expression (4), the approximate expression of the following Expression (9) is obtained.

$$R(\rho) \approx \frac{S_0}{2\pi\mu_s'}\left(\mu_{eff} + \frac{1}{\rho}\right)\frac{1}{\rho^2}e^{-\mu_{eff}\rho} \quad \text{[Expression 9]}$$

Here, regarding irradiation-detection distance $\rho$ and effective attenuation coefficient $\mu_{eff}$, when the relationship of the following Expression (10) is satisfied, Expression (9) is expressed as the following Expression (11). Here it is assumed that $\mu_{eff}$=5.77 mm ($\mu_s'$=1/mm, $\mu_a$=0.01/mm).

$$\rho \ll \frac{1}{\mu_{eff}} \quad \text{[Expression 10]}$$

$$R(\rho) = \frac{S_0}{2\pi\mu_s'}\frac{1}{\rho^3}e^{-\mu_{eff}\rho} \quad \text{[Expression 11]}$$

When Expression (11) is expressed in a logarithmic expression, Expression (1) is derived.

In addition, regarding irradiation-detection distance ρ and effective attenuation coefficient $\mu_{eff}$, when the relationship of the following Expression (12) is satisfied, Expression (9) is expressed as the following Expression (13).

$$\rho \gg \frac{1}{\mu_{eff}} \quad \text{[Expression 12]}$$

$$R(\rho) = \frac{S_0}{2\pi} \frac{3\mu_a}{\mu_{eff}} \frac{1}{\rho^2} e^{-\mu_{eff}\rho} \quad \text{[Expression 13]}$$

When Expression (13) is expressed in a logarithmic expression, Expression (2) is derived.

It is to be noted that intensity/distance calculation section 41 is not limited to the configuration using Expression (1) and Expression (2) as the present embodiment, and is appropriately selected. For example, it is possible to adopt a configuration in which detected light intensity R (ρ) and scattering coefficient $\mu_s'$ are simply in proportion to each other.

In addition, intensity/distance calculation section 41 is not limited to the configuration in which detection position 33 is provided at one point. In actual measurement, a large amount of noise may be generated. In such case, by providing multiple detection positions 33, a scattering coefficient may be derived from consecutive light intensities corresponding to irradiation-detection distances ρ. That is, in intensity/distance calculation section 41, when the noise amount of measurement data obtained at a few measurement points is relatively large, the influence of the noise assumed in actual measurement can be alleviated by increasing the number of detection positions 33.

Next, light intensity ratio calculation unit 42 is configured to calculate scattering coefficient $\mu_s'$ from ratios of light intensities detected by a plurality of light intensity detectors 3. Basically, as with light intensity/distance calculation unit 41, light intensity ratio calculation unit 42 calculates scattering coefficient $\mu_s'$ based on a scattering phenomenon in which emitted light is attenuated by scattering as the distance to the detection position 33 is increased.

In the present embodiment, consecutive light having a given light intensity is emitted by irradiator 2, and first irradiation-detection distance $\rho_1$ from irradiation position 21 to first detection position 331 of first light intensity detector 31, second irradiation-detection distance $\rho_2$ from irradiation position 21 to second detection position 332 of second light intensity detector 32, first light intensity R ($\rho_1$) detected by first light intensity detector 31, and second light intensity R ($\rho_2$) detected by second light intensity detector 32 are applied into the following Expression (3) to calculate scattering coefficient $\mu_s'$.

$$\mu_s' = \frac{1}{3\mu_a} \left\{ \frac{1}{\rho_2 - \rho_1} \ln \frac{\rho_1^2 R(\rho_1)}{\rho_2^2 R(\rho_2)} \right\}^2 \quad \text{[Expression 3]}$$

It is to be noted that Expression (3) is derived as follows.

First, in Expression (13), when light intensity R ($\rho_1$) and light intensity R ($\rho_2$) at points separated by different distances $\rho_1$ and $\rho_2$ from irradiation position 21 are measured, scattering coefficient $\mu_s'$ of a light propagation region in a living body is expressed as the following Expression (14).

$$\frac{R(\rho_2)}{R(\rho_1)} = \frac{\rho_1^2}{\rho_2^2} e^{-\mu_{eff}(\rho_2 - \rho_1)} \quad \text{[Expression 14]}$$

When Expression (14) is expressed in a logarithmic expression, the following Expression (15) is obtained.

$$\mu_{eff} = \frac{1}{\rho_2 - \rho_1} \ln \frac{\rho_1^2 R(\rho_1)}{\rho_2^2 R(\rho_2)} \quad \text{[Expression 15]}$$

When Expression (8) is applied into Expression (15), Expression (3) is derived.

As described, with Expression (3), the number of detection positions 33 can be reduced, and thus the size of the apparatus can be reduced. Consequently the apparatus can be manufactured at low cost to be suitable for home-use.

It is to be noted that the configuration of light intensity ratio calculation unit 42 is not limited to the configuration using Expression (3) as the present embodiment, and may be appropriately selected. Alternatively, a configuration may be adopted in which the attenuation rate of the distance between first detection position 331 and second detection position 332 is calculated and scattering coefficient $\mu_s'$ is calculated based on the calculated attenuation rate.

In addition, the apparatus using Expression (3) is not limited to home-use, and may be an apparatus for medical use or clinical use.

Light intensity difference calculation unit 43 is configured to calculate scattering coefficient $\mu_s'$ from the difference between light intensities detected by a plurality of light intensity detectors 3. This scattering coefficient $\mu_s'$ is obtained by calculating the difference between two points corresponding to the distance of detection positions 33, and by using the calculated value as scattering coefficient $\mu_s'$. That is, as with light intensity/distance calculation unit 41 and light intensity ratio calculation unit 42, light intensity difference calculation unit 43 calculates scattering coefficient $\mu_s'$ based on a scattering phenomenon in which emitted light is attenuated by scattering as the distance to the detection position 33 is increased.

Light intensity difference calculation unit 43 in the present embodiment acquires light intensity R ($\rho_1$) and light intensity R ($\rho_2$) at first detection position 331 and second detection position 332, calculates the difference therebetween, and uses the calculated value as scattering coefficient $\mu_s'$.

Attenuation time calculation unit 44 is configured to calculate scattering coefficient $\mu_s'$ from the period until the light intensity detected by light intensity detector 3 is attenuated to a given intensity after pulsed light is emitted by irradiator 2. That is, attenuation time calculation unit 44 calculates scattering coefficient $\mu_s'$ based on a scattering phenomenon in which emitted pulsed light is attenuated by scattering with time.

Therefore, the light intensity detected here contains information of light scattering corresponding to the concentration of lipid in blood, and information of attenuation of light intensity that is facilitated as the time from emission to detection is elongated. Thus, attenuation time calculation unit 44 acquires scattering coefficient corresponding to the blood lipid concentration from attenuation of the light intensity.

Attenuation time calculation unit 44 in the present embodiment acquires the light intensities at irradiation position 21 and detection position 33 adjacent thereto, calculates the period until the light intensity is attenuated to a given light intensity, and uses the calculated value as scattering coefficient $\mu_s'$.

Highest intensity time calculation unit 45 is configured to calculate scattering coefficient $\mu_s'$ from the period until the light intensity detected by light intensity detector 3 reaches a highest value after pulsed light is emitted by irradiator 2. That is, as with attenuation time calculation unit 414, highest intensity time calculation unit 45 calculates scattering coefficient $\mu_s'$ based on a scattering phenomenon in which emitted pulsed light is attenuated by scattering with time.

In the present embodiment, as described above, a given distance is provided between irradiation position 21 and detection position 33, and scattering occurs within the distance. Therefore, there is a time lag before the highest light intensity is detected by light intensity detector 3. Highest intensity time calculation unit 45 utilizes the time lag to acquire scattering coefficient $\mu_s'$ corresponding to blood lipid concentration.

Highest intensity time calculation unit 45 in the present embodiment acquires the light intensities at irradiation position 21 and detection position 33 adjacent thereto, calculates the period until a highest light intensity is obtained, and uses the calculated value as scattering coefficient $\mu_s'$.

Light-density waveform calculation unit 46 is configured to calculate scattering coefficient $\mu_s'$ and the absorption coefficient of blood from the light density waveform. The waveform of a light density waveform is changed by modulating the intensity or phase of light emitted by irradiator 2. Such a change of a light density waveform corresponds to the blood concentration, and therefore scattering coefficient $\mu_s'$ and the absorption coefficient of blood can be calculated therefrom.

Light-density waveform calculation unit 46 in the present embodiment acquires light intensities at irradiation position 21 and detection position 31a adjacent thereto, calculates the time variation of the light density waveform, and calculates scattering coefficient $\mu_s'$ and the absorption coefficient of blood from the calculated time variation.

It is to be noted that the method of calculating scattering coefficient $\mu_s'$ of scattering coefficient calculator 4 is not limited to the above-mentioned calculation, and may be appropriately selected from methods of calculating information of the blood lipid concentration contained in light intensity.

Lipid concentration calculator 5 is configured to calculate the blood lipid concentration based on scattering coefficient $\mu_s'$ calculated by scattering coefficient calculator 4. Although described later in Example 5, scattering coefficient $\mu_s'$ and the lipid concentration correlate with each other, and lipid concentration calculator 5 calculates the lipid concentration based on the value of scattering coefficient $\mu_s'$. In the present embodiment, the statistical data on the relationship between scattering coefficient $\mu_s'$ and the blood lipid concentration is obtained, and scattering coefficient $\mu_s'$ is compared with the statistical data to calculate the actual blood lipid concentration.

For example, when the blood lipid concentration of a certain living body, Mr. A, is the measurement object, the concentration can be calculated by comparing the measurement result of the blood lipid concentration of Mr. A, which is measured by other blood lipid concentration measurement methods or the like such as blood collection, with the calculated scattering coefficient $\mu_s'$ to prepare personal statistical data of Mr. A.

Alternatively, personal statistical data of Mr. A may be prepared by comparing the measured blood lipid concentration of Mr. A, which is acquired by a different method of measuring blood lipid concentration or the like, with the measured concentration acquired from the detected light intensity, by calculating the error between the concentration acquired from the comparison and the concentration of a common living body in the statistical data, and by performing calibration for correcting the error.

It is to be noted that the format of the statistical data is not limited, and may be classified by, for example, gender, height, weight, BMI and the like, or may be calculated using tables, graphs, function expressions and the like.

In addition, in clinical sites, the terms "concentration" may sometimes be synonymous with the term "turbidity," and the term "concentration" used in the present embodiment of the present invention includes the concept of turbidity. Therefore, the results of calculation of the lipid concentration calculator may be in the form of formazin turbidity or the particle number per unit quantity, as well as the concentration.

Next, a configuration of non-invasive biolipid metabolism measuring device 10 is described. Non-invasive biolipid metabolism measuring device 10 is configured to acquire scattering coefficient $\mu_s'$ or the lipid concentration, or both calculated by non-invasive biolipid concentration measuring device 1 to measure the biolipid metabolism from the time variation thereof. As illustrated in FIG. 1, non-invasive biolipid metabolism measuring device 10 in the present embodiment is connected with non-invasive biolipid concentration measuring device 1 through a communication line and the like.

Non-invasive biolipid metabolism measuring device 10 includes calculated-value acquirer 101 that acquires scattering coefficient $\mu_s'$ and the lipid concentration calculated by non-invasive biolipid concentration measuring device 1 at specified time intervals, and biolipid metabolism determinator 102 that determines the biolipid function based on the time variation of scattering coefficient $\mu_s'$ and the lipid concentration acquired by calculated-value acquirer 101.

Calculated-value acquirer 101 is configured to acquire scattering coefficient $\mu_s'$ and the lipid concentration calculated by non-invasive biolipid concentration measuring device 1 through a communication line or the like at specified time intervals. Time intervals of the acquisition are not limited, and may be adjusted to intervals of several seconds, several tens of minutes, or more in accordance with the examination object.

It is to be noted that scattering coefficient $\mu_s'$ and the lipid concentration may not be acquired through a communication line, and may be acquired by manually inputting the value of the lipid concentration and the like calculated by non-invasive biolipid concentration measuring device 1. In addition, while non-invasive biolipid concentration measuring device 1 and non-invasive biolipid metabolism measuring device 10 are separately provided in the present embodiment, this is not limitative. Non-invasive biolipid concentration measuring device 1 and non-invasive biolipid metabolism measuring device 10 may be integrally configured, or one of the measuring devices may have the other's function.

Biolipid metabolism determination determinator 102 is configured to determine the biolipid metabolism of the examinee from the time variation of scattering coefficient $\mu_s'$ and the lipid concentration acquired by calculated-value acquirer 101. For example, since the period until scattering coefficient $\mu_s'$ and the lipid concentration maximum value reach a highest value corresponds to digestion and absorption of lipid by stomach and small intestine, the health condition is determined based on the time length. In addition, lipolysis effect of liver is determined from the period until scattering coefficient $\mu_s{'}$ and the lipid concentration reach the values of the fasting state. Finally, the above-mentioned factors are comprehensively determined to generally determine the health condition.

Next, the following describes operations of a method of non-invasively measuring biolipid concentration and a method of non-invasively examining biolipid metabolism using non-invasive biolipid concentration measuring device 1 and non-invasive biolipid metabolism measuring device 10 of the present embodiment.

First, effects of non-invasive biolipid concentration measuring device 1 and the method of non-invasively measuring biolipid concentration are described for each unit of scattering coefficient calculator 4.

"Concentration Measurement Using Light Intensity/Distance Calculation Unit 411"

An irradiation process in the present embodiment is performed using irradiator 2 of non-invasive biolipid concentration measuring device 1. In the case of concentration measurement using light intensity/distance calculation unit 41, irradiator 2 emits consecutive light having given light intensity $S_0$ toward the inside of the body from outside to irradiate irradiation position 21 with the consecutive light. By using consecutive light to irradiate the living body, the influence of the attenuation with time is prevented from being contained in the light intensity detected by light intensity detector 3.

In addition, in the present embodiment, the light source emits light having wavelengths which do not fall within the wavelength range within which the light is absorbed by inorganic substances of plasma and the wavelength range within which light is absorbed by cell components of blood. Thus, when light passes through the blood, light absorption of inorganic substances of plasma and cell components of blood is limited, and the influence of scattering of blood lipid is left in the light intensity detected by light intensity detector 3.

A light intensity detection process in the present embodiment is performed using light intensity detector 3 of non-invasive biolipid concentration measuring device 1. In the present embodiment, first light intensity detector 31 detects the light intensity at first detection position 331. The light intensity thus detected is passed on to a scattering coefficient calculation process.

The scattering coefficient calculation process in the present embodiment is performed using light intensity/distance calculation unit 41 of scattering coefficient calculator 4 in non-invasive biolipid concentration measuring device 1. In light intensity/distance calculation unit 41, as described above, the light intensity detected in the light intensity detection process, that is, light intensity R ($\rho$), and irradiation-detection distance $\rho$ are applied into the following Expression (1) and Expression (2) to calculate scattering coefficient $\mu_s{'}$. Scattering coefficient $\mu_s{'}$ thus calculated is passed on to a lipid concentration calculation process.

$$\ln\left\{\rho^2 \frac{R(\rho)}{S_0}\right\} = -\mu_{\mathit{eff}}\rho + \ln\frac{3\mu_a}{2\pi\mu_{\mathit{eff}}} \qquad \text{[Expression 1]}$$

$$\ln\left\{\rho^3 \frac{R(\rho)}{S_0}\right\} = -\mu_{\mathit{eff}}\rho + \ln\frac{1}{2\pi\mu_s{'}} \qquad \text{[Expression 2]}$$

The lipid concentration calculation process is performed using lipid concentration calculator 5 in non-invasive biolipid concentration measuring device 1. In lipid concentration calculator 5, based on a correlation between the blood lipid concentration and scattering coefficient $\mu_s{'}$, the scattering coefficient $\mu_s{'}$ is multiplied by a given coefficient to calculate the blood lipid concentration and the like.

That is, with scattering coefficient calculator 4 and the scattering coefficient calculation process in the present embodiment, scattering coefficient $\mu_s{'}$ can be instantly acquired by acquiring a light intensity and applying the acquired light intensity into a given expression. In addition, with lipid concentration calculator 5 and the lipid concentration calculation process, blood lipid concentration, turbidity or the like can be readily calculated by multiplying the scattering coefficient $\mu_s{'}$ by a given coefficient. Consequently, the arithmetic processing speed is increased, and real time measurement can be achieved.

"Concentration Measurement Using Light Intensity Ratio Calculation Unit 42"

In the irradiation process, as with light intensity/distance calculation unit 41, irradiation position 21 is irradiated with consecutive light with use of irradiator 2.

In the light intensity detection process, the light intensity at first detection position 331 is detected using first light intensity detector 31, and the light intensity of second detection position 332 is detected using second light intensity detector 32. The light intensities detected at first detection position 331 and second detection position 332 are passed on to a scattering coefficient calculation process.

In the scattering coefficient calculation process, light intensity ratio calculation unit 42 of scattering coefficient calculator 4 calculates the ratio of the acquired light intensities of first detection position 331 and second detection position 332, and calculates scattering coefficient $\mu_s{'}$ from the ratio. In the present embodiment, first irradiation-detection distance $\rho_1$ from irradiation position 21 to first detection position 331 of first light intensity detector 31, second irradiation-detection distance $\rho_2$ from irradiation position 21 to second detection position 332 of second light intensity detector 32, first light intensity R ($\rho_1$) detected by first light intensity detector 31, and second light intensity R ($\rho_2$) detected by second light intensity detector 32 are applied into the following Expression (3) to calculate scattering coefficient $\mu_s{'}$. Scattering coefficient $\mu_s{'}$ thus calculated is passed on to a lipid concentration calculation process.

$$\mu_s' = \frac{1}{3\mu_a}\left\{\frac{1}{\rho_2 - \rho_1}\ln\frac{\rho_1^2 R(\rho_1)}{\rho_2^2 R(\rho_2)}\right\}^2 \qquad \text{[Expression 3]}$$

The lipid concentration calculation process is performed using lipid concentration calculator 5 in non-invasive biolipid concentration measuring device 1. In lipid concentration calculator 5, scattering coefficient $\mu_s{'}$ is multiplied by a given coefficient to calculate the blood lipid concentration and the like.

"Concentration Measurement Using Light Intensity Difference Calculation Unit 43"

As with light intensity/distance calculation unit 41 and light intensity ratio calculation unit 42, in the irradiation process, irradiation position 21 is irradiated with consecutive light using irradiator 2, and in the light intensity detection process, the light intensity at first detection position 331 is detected using first light intensity detector 31 whereas the light intensity of second detection position 332 is detected using second light intensity detector 32. The light intensities detected at first detection position 331 and second detection position 332 are passed on to a scattering coefficient calculation process.

In the scattering coefficient calculation process, the difference between the first light intensity at first detection position 331 and the second light intensity at second detection position 332 is calculated, and the difference is used as scattering coefficient $\mu_s'$. Scattering coefficient $\mu_s'$ thus calculated is passed on to a lipid concentration calculation process.

The lipid concentration calculation process is performed using lipid concentration calculator 5 in non-invasive biolipid concentration measuring device 1. In lipid concentration calculator 5, scattering coefficient $\mu_s'$ is multiplied by a given coefficient to calculate the blood lipid concentration and the like.

"Concentration Measurement Using Attenuation Time Calculation Unit 44"

In the irradiation process, irradiation position 21 is irradiated with pulsed light by irradiator 2. By using pulsed light for irradiation of a living body, the influence of the attenuation with time is contained in the light intensity detected by light intensity detector 3.

In the light intensity detection process, the light intensity of first detection position 331 is detected in a temporally continuous manner using first light intensity detector 3. Then, the light intensity detected at first detection position 331 is passed on to a scattering coefficient calculation process at specified time intervals.

In the scattering coefficient calculation process, attenuation time calculation unit 44 acquires the light intensity at first detection position 331 at specified time intervals, and determines whether the acquired light intensity has been attenuated to a given light intensity or lower. When it is determined that the light has been attenuated, the time length from the time when the pulsed light is emitted by irradiator 2 to the time when the light is determined to be attenuated is calculated, and the time length thus calculated is used as scattering coefficient $\mu_s'$. Scattering coefficient $\mu_s'$ thus calculated is passed on to a lipid concentration calculation process.

The lipid concentration calculation process is performed using lipid concentration calculator 5 in non-invasive biolipid concentration measuring device 1. In lipid concentration calculator 5, the scattering coefficient $\mu_s'$ is compared with preliminarily prepared statistical data to calculate the blood lipid concentration and the like.

"Concentration Measurement Using Highest Intensity Time Calculation Unit 45"

As with attenuation time calculation unit 44, in the irradiation process, irradiation position 21 is irradiated with pulsed light using irradiator 2. In the light intensity detection process, the light intensity of first detection position 331 is detected in a temporally continuous manner using first light intensity detector 31. Then, the light intensity detected at first detection position 331 is passed on to a scattering coefficient calculation process at specified time intervals.

In the scattering coefficient calculation process, highest intensity time calculation unit 45 acquires the light intensity at first detection position 331 at specified time intervals, and determines whether the light intensity has a high value. When it is determined that the light intensity has a highest value, the time length from the time when the pulsed light is emitted by irradiator 2 to the time when the light is determined to have a highest value is calculated, and the time length thus calculated is used as scattering coefficient $\mu_s'$. Scattering coefficient $\mu_s'$ thus calculated is passed on to a lipid concentration calculation process.

The lipid concentration calculation process is performed using lipid concentration calculator 5 in non-invasive biolipid concentration measuring device 1. In lipid concentration calculator 5, scattering coefficient $\mu_s'$ is compared with preliminarily prepared statistical data to calculate the blood lipid concentration and the like.

"Concentration Measurement Using Light-Density Waveform Calculation Unit 46"

In the irradiation process, light obtained by modulating the intensity or phase of the light emitted to irradiation position 21 is emitted. In the light intensity detection process, the light intensity of first detection position 331 is detected using first light intensity detector 31. The light intensity detected at first detection position 331 is passed on to a scattering coefficient calculation process at specified time intervals.

In the scattering coefficient calculation process, light-density waveform calculation unit 46 acquires the light intensity at first detection position 331 at specified time intervals, calculates a light density waveform, and calculates the scattering coefficient $\mu_s'$ and the absorption coefficient of blood based on the light density waveform. Scattering coefficient $\mu_s'$ thus calculated is passed on to a lipid concentration calculation process.

The lipid concentration calculation process is performed using lipid concentration calculator 5 in non-invasive biolipid concentration measuring device 1. In lipid concentration calculator 5, scattering coefficient $\mu_s'$ and the absorption coefficient calculated by light-density waveform calculation unit 46 are compared with preliminarily prepared statistical data to calculate the blood lipid concentration and the like.

The following describes effects of non-invasive biolipid metabolism measuring device 10 and the non-invasive biolipid metabolism measurement method.

First, a calculation value acquiring process of the non-invasive biolipid metabolism measurement method is performed using calculated-value acquirer 101 of non-invasive biolipid metabolism measuring device 10. Calculated-value acquirer 101 accesses non-invasive biolipid concentration measuring device 1 to acquire calculated scattering coefficient $\mu_s'$ and the lipid concentration through a communication line at specified time intervals. In the present embodiment, both of scattering coefficient $\mu_s'$ and the lipid concentration are acquired and passed on to a biolipid function metabolism determination process.

The biolipid function metabolism determination process is performed using biolipid metabolism determinator 102 of non-invasive biolipid metabolism measuring device 10. Biolipid metabolism determinator 102 monitors time-series changes of the acquired scattering coefficient $\mu_s'$ and lipid concentration, and acquires a given value representing the biolipid metabolism. In the present embodiment, the maximum values of scattering coefficient $\mu_s'$ and the lipid concentration, the period until the maximum values are reached, and the period until the value of the fasting state is reached through the maximum values, are acquired.

Then, the values are compared with preliminarily prepared statistical data, and when the values are determined to be normal values, it is determined that the values are normal values, and when the values are determined to fall outside normal values, it is determined that abnormality of biolipid metabolism is present.

For example, when maximum values of scattering coefficient $\mu_s'$ and the lipid concentration are normal values, it is determined that the basic metabolism of lipid is normal, and when maximum values of scattering coefficient $\mu_s'$ and the lipid concentration are not normal values, it is determined that the basic metabolism of lipid is abnormal. Likewise, when the period until scattering coefficient $\mu_s'$ and the lipid concentration reaches the maximum value are normal values, it is determined that the function of digestion and absorption of lipid by stomach and small intestine is normal, and when the period until scattering coefficient $\mu_s'$ and the lipid concentration reaches the maximum value are not normal values, it is determined that the function of digestion and absorption of lipid by stomach and small intestine is abnormal for some reason. In addition, when the period until scattering coefficient $\mu_s'$ and the lipid concentration reach the values of the fasting state are normal values, it is determined that lipolysis effect of liver is normal, and when the period until scattering coefficient $\mu_s'$ and the lipid concentration reach the values of the fasting state are not normal values, it is determined that lipolysis effect of the liver is abnormal.

In clinical sites, the above-mentioned normality and abnormality are comprehensively determined, and thus health condition is comprehensively determined.

With the above-mentioned non-invasive biolipid concentration measuring device 1, non-invasive biolipid metabolism measuring device 10, the method of non-invasively measuring biolipid concentration, and the method of non-invasively examining biolipid metabolism of the present embodiment, the following effects are achieved.

1. The blood lipid concentration can be non-invasively acquired by determining scattering coefficient $\mu_s'$ in a living body based on the light intensity.
2. Invasive operations such as blood collection are not required, and thus pain and risk of the examinee can be reduced.
3. The blood lipid can be measured at home since medical acts such as blood collection are not required.
4. Data can be instantly acquired since the processes of calculating light intensity scattering coefficient $\mu_s'$ and the lipid concentration are simple.
5. Application to examination of metabolic errors such as postprandial hyperlipidemia can be achieved since blood lipid and scattering coefficient $\mu_s'$ well correlated with the blood lipid can be calculated in a temporally continuous manner.
6. The accuracy of measurement of the blood lipid concentration can be enhanced by setting the wavelength range of light to be emitted to a living body to a range falling outside the wavelength range within which light is absorbed by inorganic substances of plasma so as to limit the influence of absorption that results in noise.
7. Blood lipid concentration measurement can be achieved more correctly by further excluding the wavelength range within which light is absorbed by cell components of blood so as to limit the influence of absorption by cell components such as red blood cell.
8. Scattering coefficient $\mu_s'$ and the lipid concentration can be calculated by various calculation methods by taking into consideration the relationship between the light scattering of blood lipid and the blood lipid concentration.
9. In lipid concentration calculator 5 or the lipid concentration calculation process, conversion to particle number, formazin turbidity or the like, as well as units such as concentration (mg/dL), are also possible in accordance with the demand in the clinical site.

EXAMPLES

<Example 1> Variation in Blood Lipid Caused by Ingestion of Lipid (1) Variation in Whole Blood First, whether the concentration of blood lipid and the like of examinees changes with time after ingestion of lipid was confirmed. The examinees are Mr. A and Mr. B, each of them ingested lipid (OFTT Cream; Jyoumou Corporation).

Figure 6:
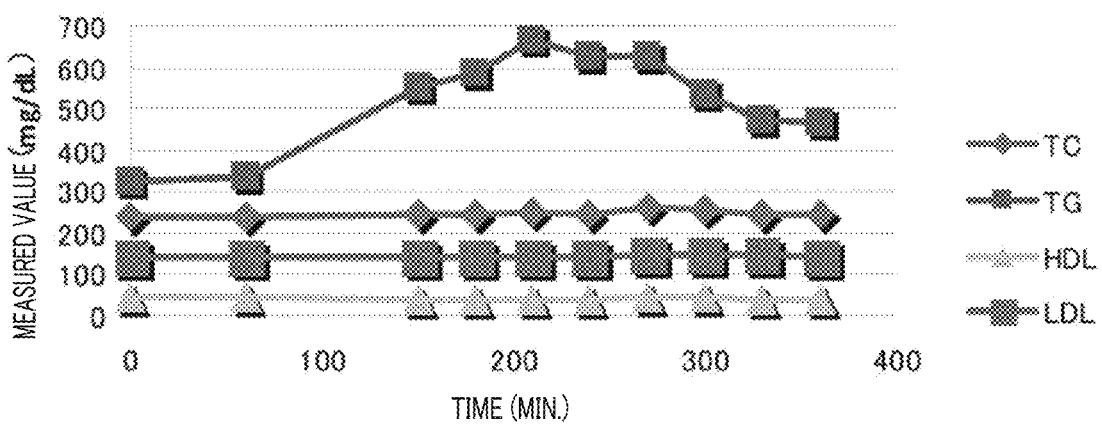
FIG. 6 is a graph showing time variation of the blood lipid concentration of Mr. A with use of a conventional method in Example 1.
Figure 7:
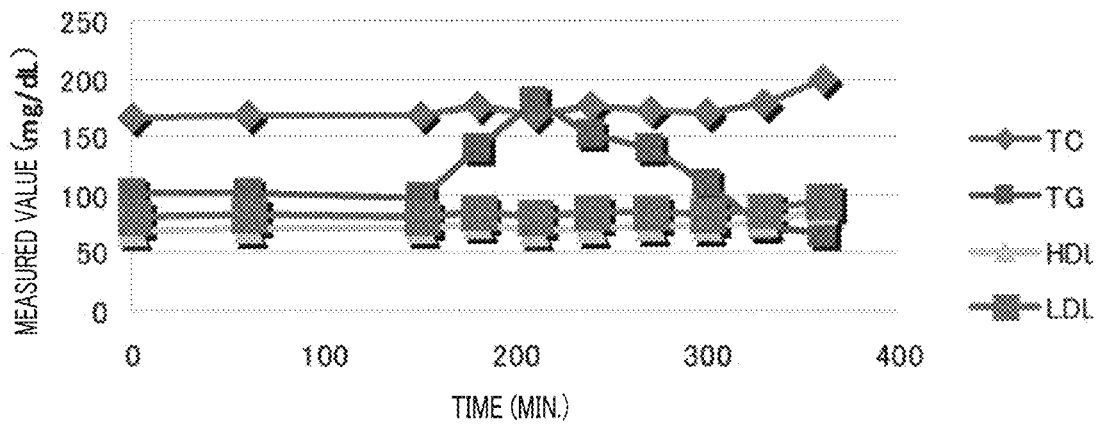
FIG. 7 is a graph showing time variation of the blood lipid concentration of Mr. B with use of a conventional method in Example 1.

The blood lipid concentration was measured as follows. At a time before ingestion of lipid (0 minute), and at 60, 150, 180, 210, 240, 270, 300, 330 and 360 minutes after ingestion, blood was collected to collect blood samples, and the blood samples were put in automatic analysis apparatus H-7170 (Hitachi High-Technologies Corporation.) to measure concentrations of total cholesterol (TC), triglyceride (TG), HDL and LDL. Results of the measurement are shown in FIG. 6 and FIG. 7. In FIG. 6 and FIG. 7, the abscissa represents the time elapsed from the examinee's ingestion of lipid, and the ordinate represents concentrations of total cholesterol (TC), triglyceride (TG), HDL and LDL.

As shown in FIG. 6 and FIG. 7, the concentrations of triglyceride (TG) of Mr. A and Mr. B were increased at 60 minutes and after 150 minutes have passed, respectively.

Meanwhile, the concentrations of total cholesterol (TC), HDL and LDL were not significantly varied. These results clearly show that ingestion of lipid results in dominant increase of the concentration of triglyceride (TG) in blood.

(2) Variations in Each Lipoprotein

Next, in order to identify the substance that contributes to increase in triglyceride (TG), the blood samples of Example 1 (1) were put in a high-performance liquid chromatography (HPLC) and fractionated into chylomicron (CM)/VLDL, LDL and HDL, and the total cholesterol (TC) and the concentration of triglyceride (TG) in CM/VLDL, LDL and HDL were measured. Results are shown in FIG. 8 to FIG. 11. In FIG. 8 to FIG. 11, the abscissa represents the time elapsed from the examinee's ingestion of lipid, and the ordinate represents the total cholesterol (TC) or the triglyceride (TG) concentration in CM/VLDL, LDL and HDL. In addition, the term "concentration of chylomicron (CM)/VLDL" refers to the total concentration of chylomicron (CM) and VLDL.

Figure 8:
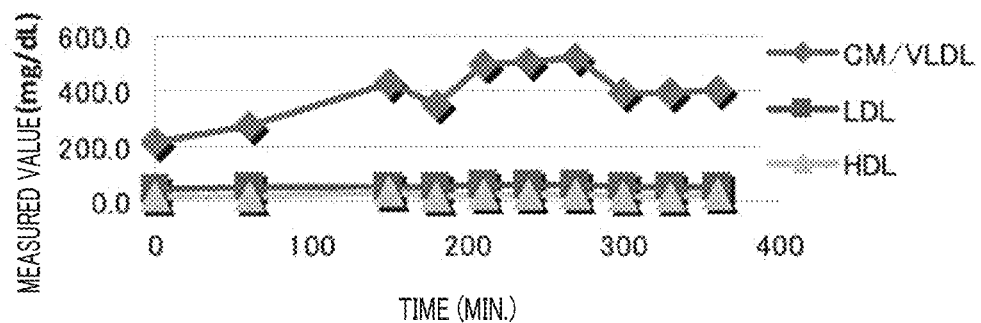
FIG. 8 is a graph showing results of measurement of the TG concentration in CM/VLDL, LDL and HDL of Mr. A with use of HPLC in Example 1.
Figure 9:
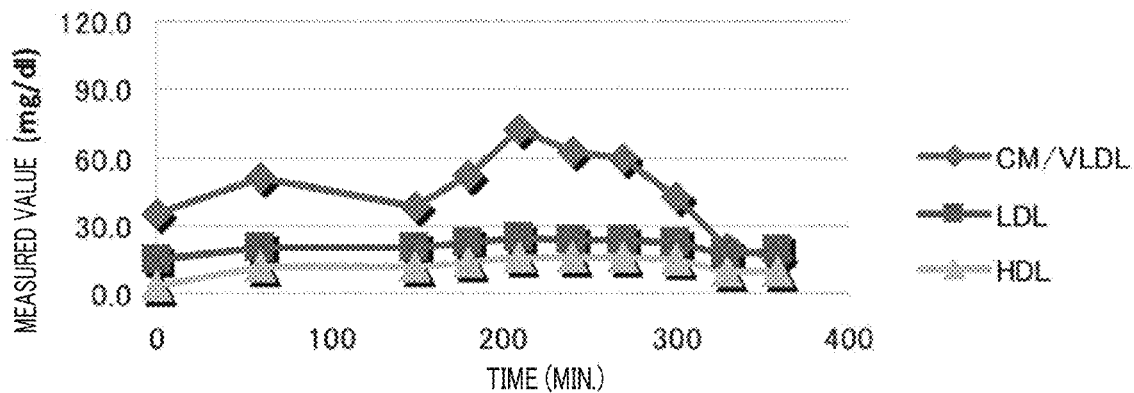
FIG. 9 is a graph showing results of measurement of the TG concentration in CM/VLDL, LDL and HDL of Mr. B with use of HPLC in Example 1.
Figure 10:
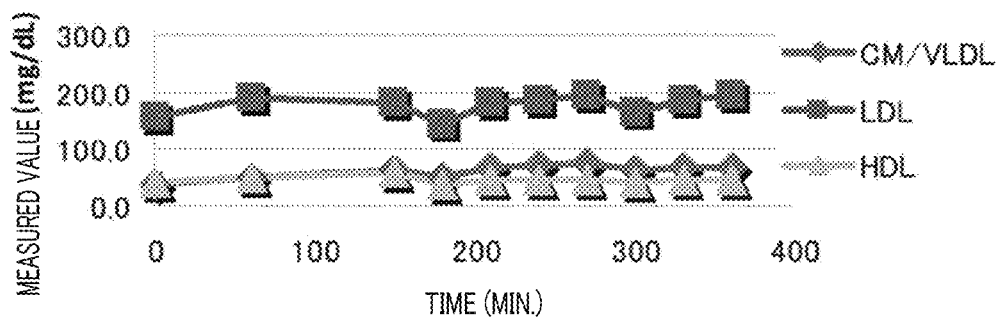
FIG. 10 is a graph showing results of measurement of the TC concentration in CM/VLDL, LDL and HDL of Mr. A with use of HPLC in Example 1.
Figure 11:
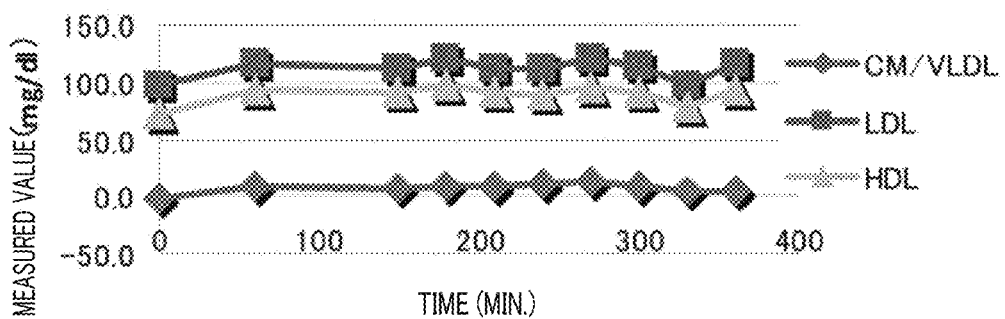
FIG. 11 is a graph showing results of measurement of the TC concentration in CM/VLDL, LDL and HDL of Mr. B with use of HPLC in Example 1.

As shown in FIG. 8 and FIG. 9, the concentrations of triglyceride (TG) in CM/VLDL of Mr. A and Mr. B increased until about 270 minutes and about 210 minutes, respectively, after ingestion of fat, whereas the concentrations of TG in LDL and HDL were not substantially varied with time. In addition, as shown in FIG. 10 and FIG. 11, the concentrations of total cholesterol (TC) in CM/VLDL, LDL and HDL were not substantially varied with time.

These results clearly show that increase in concentration of triglyceride (TG) in blood caused after ingestion of fat was caused by increase in TG in large lipoprotein such as CM/VLDL, when the results that total cholesterol (TC) and triglyceride (TG) of LDL and HDL were not substantially varied are taken into consideration.

<Example 2> Studies on Wavelength

Figure 12:
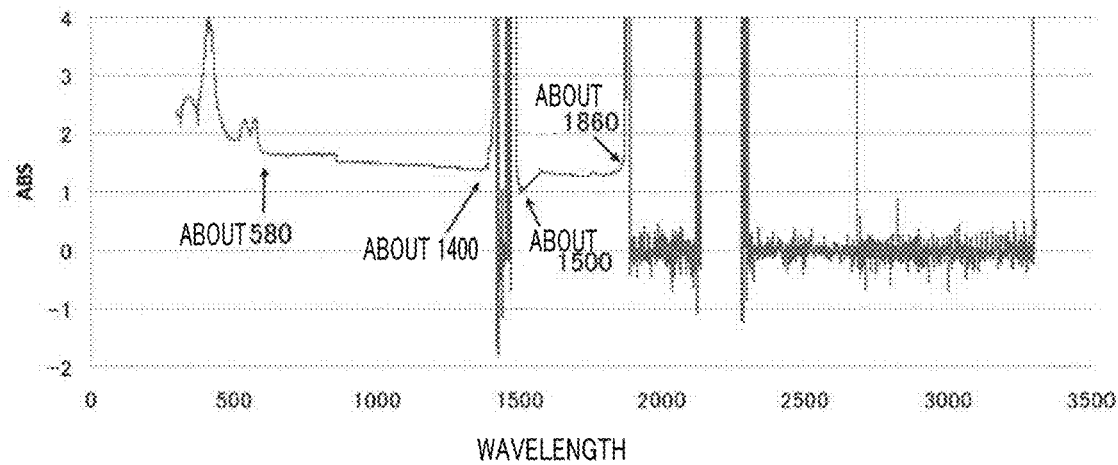
FIG. 12 is a graph showing results of measurement of the light absorption spectrum of blood with use of a spectrophotometer in Example 2.

Next, in Example 2, measurable wavelength ranges when light is non-invasively emitted toward the inside of the body from outside to determine scattering coefficient $\mu_s'$ from the intensity of light emitted to the outside of the body were studied. In this study, blood was collected from an examinee, and whole blood was put in a spectrophotometer to measure the light absorbance of the blood with light having wavelengths of 300 to 3300 nm, thereby obtaining the absorption spectrum. Results are shown in FIG. 12. In FIG. 12, the abscissa represents the light wavelength, and the ordinate represents the light absorbance.

As shown in FIG. 12, at wavelengths of about 1400 to 1500 nm and at wavelengths of about 1860 nm or longer, the light absorbance varied vertically. One possible reason for this is that the light of the above-mentioned wavelength ranges is greatly influenced by the absorption by inorganic substances of plasma. That is, when light of the wavelength ranges is used, it is unclear whether decrease in intensity of detected light with respect to emitted light is caused by absorption or scattering because of the great variation in light absorbance. This clearly shows that the wavelength of light used for measurement of the blood lipid concentration preferably falls within the range of about 1400 nm or shorter and the range of about 1500 to 1860 nm within which the influence of light absorption by inorganic substances of plasma is small. In addition, in the range of about 580 nm or smaller, the influence of light absorption by cell components of blood was found. This clearly shows that the wavelength of light used for measurement of the blood lipid concentration preferably falls within the range of about 580 nm to about 1400 nm, and the range of about 1500 to 1860 nm.

<Example 3> Studies on Transmitted Light

Next, in Example 3, effectiveness of measurement using transmitted light, and measurement of the blood lipid concentration by non-invasively emitting light toward the inside of the body from outside so as to determine scattering coefficient $\mu_s'$ from the intensity of light emitted to the outside of the body was studied.
(1) Variation in Light Absorbance of Blood, Blood Cells and Serum in Association with Change in Lipid Concentration First, by the method of (1) of Example 1, a blood sample of Mr. A was prepared and the blood lipid concentration was measured. Results are shown in Table 1.

TABLE 1

|  | TC | TG | HDL | LDL |
|---|---|---|---|---|
| Mr. A | 271.1 | 390.1 | 52.6 | 166.5 |
|  | 274.1 | 408.4 | 51.5 | 164.9 |
|  | 262.7 | 518.2 | 47.4 | 154.7 |
|  | 274.2 | 499.6 | 48.1 | 161.2 |

Here, blood samples shown in Table 1 having triglyceride (TG) concentration of 390.1, 408.4, 518.2 and 499.6 mg/dL are referred to as samples a, b, c and d, respectively.

Figure 13:
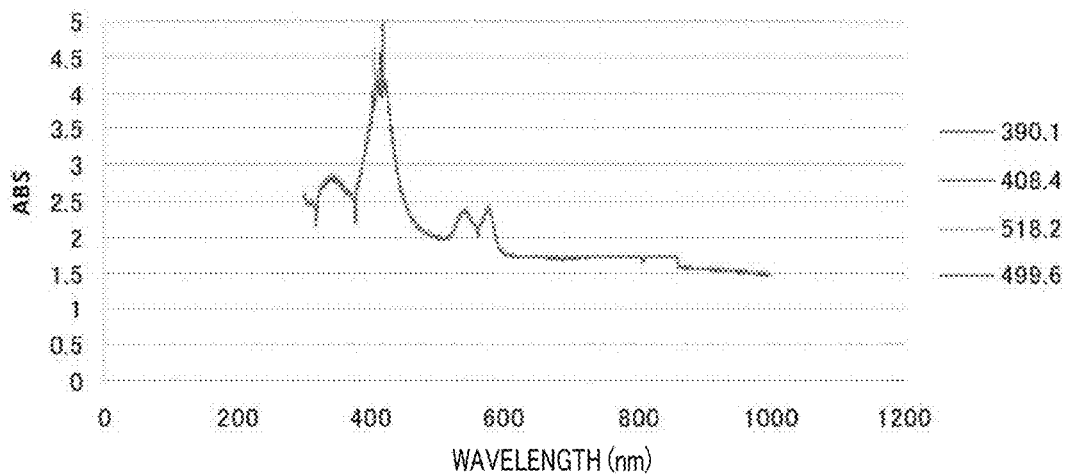
FIG. 13 is a graph showing results of measurement of the light absorption spectrums of blood of samples a, b, c and d with use of a spectrophotometer in Example 3.
Figure 14:
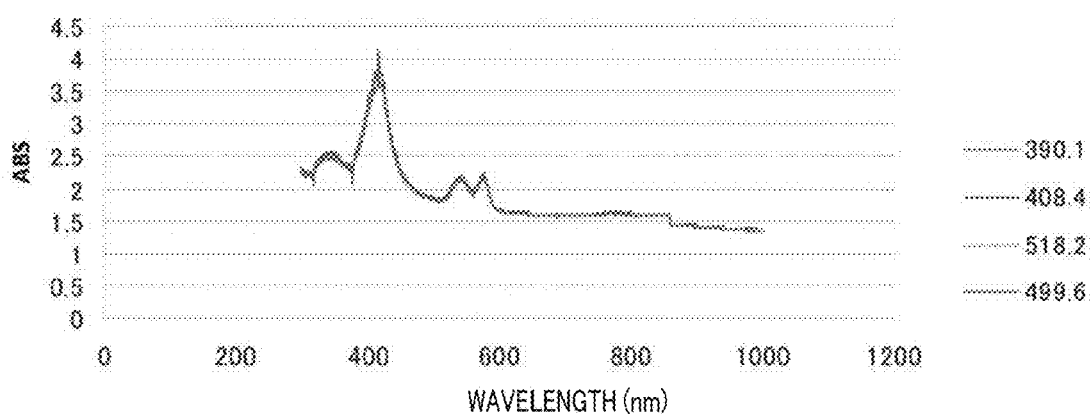
FIG. 14 is a graph showing results of measurement of the light absorption spectrums of blood cells of samples a, b, c and d with use of a spectrophotometer in Example 3.
Figure 15:
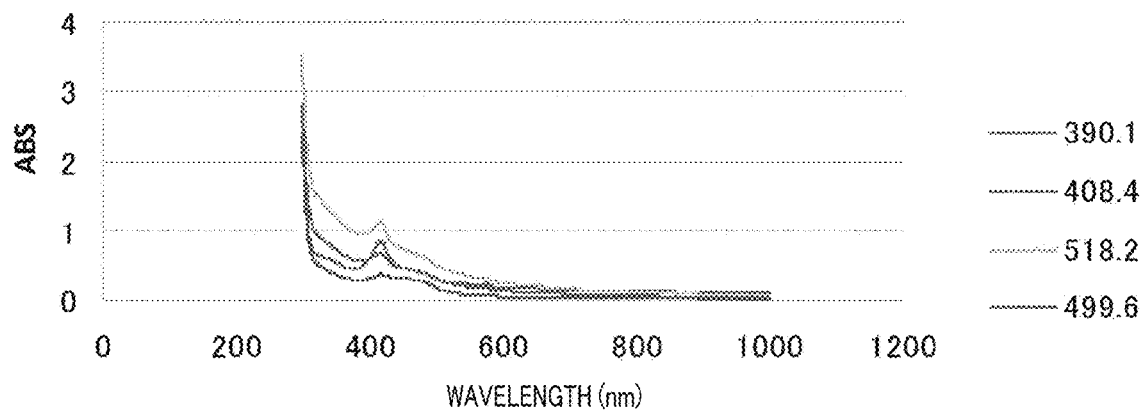
FIG. 15 is a graph showing results of measurement of the light absorption spectrums of serum of samples a, b, c and d with use of a spectrophotometer in Example 3.

Subsequently, samples a, b, c and d are put in a spectrophotometer, and the light absorbance of blood with respect to light having a wavelength of 300 to 1000 nm was measured to obtain absorption spectrums. Likewise, serum and blood cells of samples a, b, c and d were also obtained, and absorption spectrums were obtained by the above-mentioned method. Results are shown in FIG. 13 to FIG. 15. In FIG. 13 to FIG. 15, the abscissa represents the light wavelength, and the ordinate represents the light absorbance.

Figure 16:
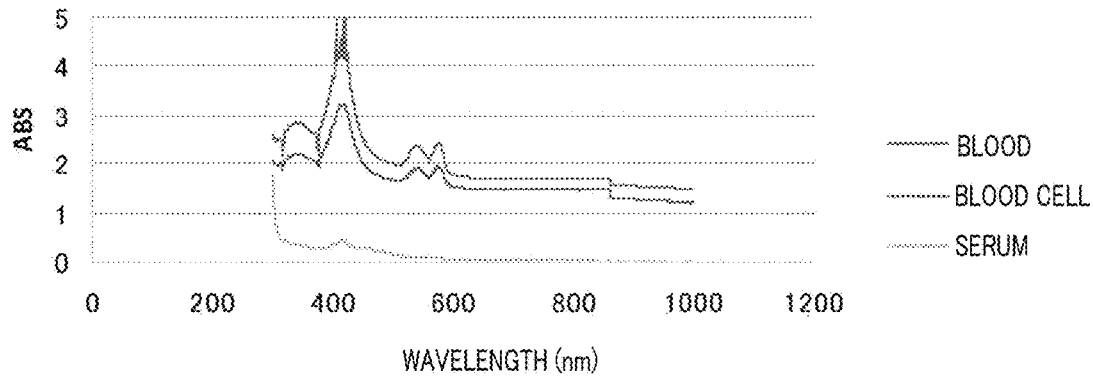
FIG. 16 is a graph showing the absorption spectrums of blood, blood cell and serum superimposed on one another in Example 3.

As shown in FIG. 13 and FIG. 14, the light absorbances of blood and blood cell were substantially the same in samples a, b, c and d. In contrast, as shown in FIG. 15, regarding the light absorbance of serum, the result of sample c> sample d> sample b> sample a was obtained. This clearly shows that the light absorbances of blood and blood cell do no vary along with the variation in lipid concentration whereas the light absorbance of serum increases along with the increase in lipid concentration. These results clearly show that serum becomes turbid when the lipid concentration increases. Thus, it was confirmed that variation in blood lipid concentration can be measured by determining scattering coefficient $\mu_s'$ representing the turbid state.
(2) Studies on Absorption Spectrum Likewise, blood was collected from Mr. A to obtain blood, blood cell and serum. The blood, blood cell and serum thus obtained were put in a spectrophotometer, and the light absorbance of blood with respect to light having a wavelength of 300 to 1000 nm was measured, thus obtaining absorption spectrums. It is to be noted that the basic principle of spectrophotometers is irradiation of a measurement object with light and analyze of transmitted light. FIG. 16 shows the absorption spectrums of blood, blood cell and serum superimposed on one another.

As shown in FIG. 16, the light absorbance of serum was significantly small in comparison with the light absorbances of blood and blood cell. This clearly shows that the light absorbance of blood reflects the light absorbance of blood cell, but does not reflect the light absorbance of serum. These results clearly show that the turbid state of serum in association with increase in lipid concentration is difficult to confirm or cannot be confirmed by detection of transmitted light of blood.

<Example 4> Measurement of Lipid Concentration Based on Time-Resolved Measurement Method In Example 4, with use of non-invasive biolipid concentration measuring device 1 of the embodiment of the present invention, whether the lipid concentration can be measured based on a scattering phenomenon in which emitted light is attenuated with time by scattering was confirmed.
(1) Studies on the Period Until Light is Completely Output (Spread of Waveform)

Irradiation position 21 was set at a center portion of an examinee's back of the hand on the skin over a blood vessel. In addition, detection position 31 is set on the skin over the blood vessel that is common to the irradiation position, at a position separated by 10 mm from irradiation position 21. Ti: Spphirelaser Chameleon Ultra II (variable wavelength type, pulse width: 140 fs FWHM, average output: 400 m W, repetition frequency: 80 MHz; Coherent Inc.) was used as light source 22 of irradiation position 21, and a streak camera was used as light intensity detector 3 of detection position 31.

Figure 17:
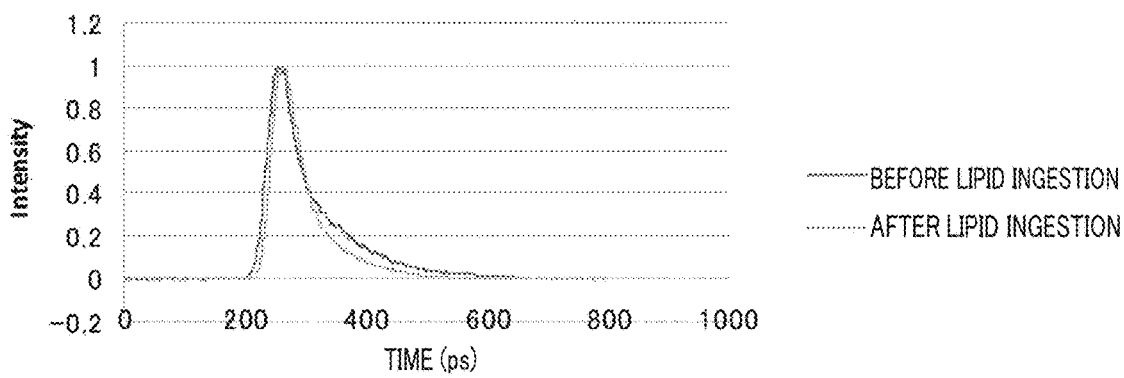
FIG. 17 is a graph showing time-series light intensities detected at a detection position in Example 4.
Figure 18:
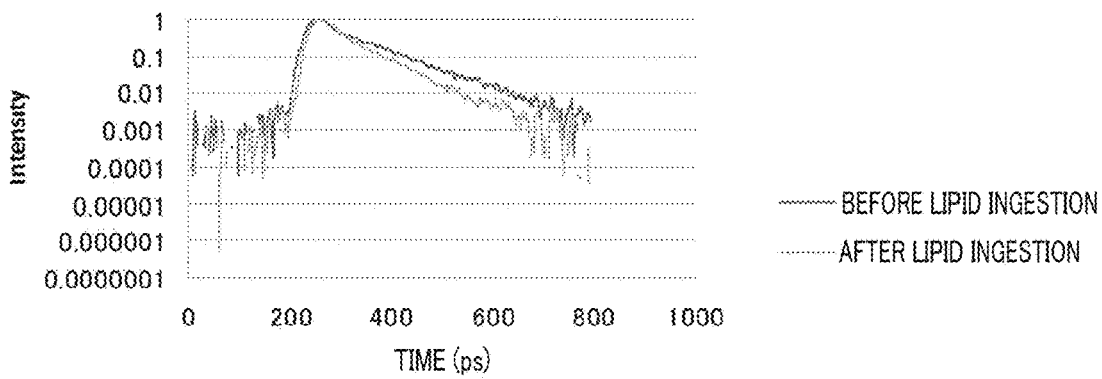
FIG. 18 is a logarithmic graph showing time-series light intensities detected at a detection position in Example 4.

Lipid was ingested by examinee, and before and after the ingestion of lipid, irradiation position 21 is irradiated with pulsed light having a wavelength of 853 nm, and the light intensity detected at detection position 31 was measured in a time dependent manner. Results are shown in FIG. 17 and FIG. 18. In FIG. 17 and FIG. 18, the abscissa represents the time elapsed from the examinee's ingestion of lipid, and the ordinate represents the light intensity.

As shown in FIG. 17 and FIG. 18, the waveform is spread after the ingestion of fat in comparison with before the ingestion of fat. That is, along with the increase in blood lipid concentration, the light scattering intensity in blood was increased. This result shows that the light intensity that has an influence on scattering was detected without blood collection by emitting light from the outside of the body and by detecting light.

(2) Studies on Peak Top Time

Figure 19:
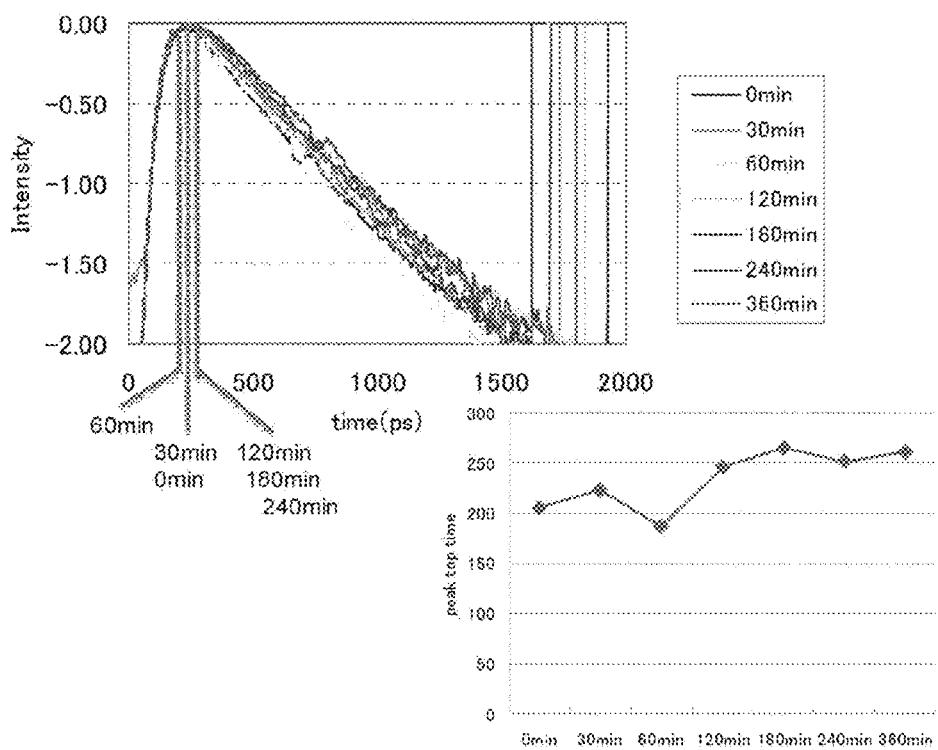
FIG. 19 is a graph showing the time (peak top time) at which the intensity of detected light is highest in Example 4.

Next, to obtain scattering coefficient $\mu_s'$, the period (peak top time) until the intensity of detected light reaches a highest value was studied. Results are shown in FIG. 19. In FIG. 19, the abscissa represents the time elapsed from the examinee's ingestion of lipid, and the ordinate represents the light intensity.

As shown in FIG. 19, after the ingestion of fat, the period until the intensity of detected light (peak top time) was prolonged in comparison with before the ingestion of fat, and these results clearly show that the light intensity in the blood was increased. That is, it can be said that light scattering in the blood is increased along with the increase in blood lipid concentration. This result shows that the blood lipid concentration can be measured without blood collection by emitting light from outside of a living body and by calculating the influence of scattering by blood lipid from the detected light intensity.

<Example 5> Measurement of Lipid Concentration Based on Space-Resolved Measurement Method Next, in Example 5, whether the lipid concentration can be measured based on a scattering phenomenon in which emitted light is attenuated in accordance with the distance by scattering using non-invasive biolipid concentration measuring device 1 of the embodiment of the present invention was determined.

(1) Measurement of Light Intensity at a Plurality of Detection Positions 33

Irradiation position 21 was set at a center portion of the back of the hand of examinees, Mr. A and Mr. B, on the skin over a blood vessel. In addition, three detection positions 33 are set on the skin over the blood vessel that is common to the irradiation positions separated from irradiation position 21 by 10 mm, 15 mm and 20 mm, respectively. Ti: Sapphire (Ti:S) laser Chameleon Ultra (automatic wavelength-sweep femtosecond laser; Coherent Inc.) was used as light source 22 of irradiation position 21, and Femtowatt Photoreceiver FWPR-20-SI (FEMTO Messtechnik GmbH) was used as light intensity detector 3 of detection position 33.

Lipid (OFTT Cream; Jyoumou Corporation) was ingested by the examinees, Mr. A and Mr. B, and at a time before the ingestion of lipid (at 0 minute), and at 60, 150, 180, 210, 240, 270, 300, 330 and 360 minutes after the ingestion of lipid, laser beams of wavelengths of 800 nm, 809 nm, 850 nm and 1000 nm were applied to irradiation position 21 and light intensities detected at respective detection positions 33 were measured. Results are shown in Table 2.

TABLE 2

|  | Mr. A | Mr. B |
|---|---|---|
| 1000-10 | 2.53155 | 3.136944444 |
| 1000-15 | 0.986388889 | 1.226483333 |
| 1000-20 | 0.680122778 | 0.601847222 |
| 1000-10 | 3.668127778 | 4.685 |
| 1000-15 | 1.072857222 | 1.956933333 |
| 1000-20 | 0.709881667 | 0.854455556 |
| 1000-10 | 3.869155556 | 3.937844444 |
| 1000-15 | 1.130229444 | 1.348988889 |
| 1000-20 | 0.693549444 | 0.694226111 |
| 1000-10 | 3.206766667 | 4.877944444 |
| 1000-15 | 1.123125556 | 1.104432778 |
| 1000-20 | 0.737665556 | 0.592620556 |
| 1000-10 | 6.39605 | 5.553061111 |
| 1000-15 | 1.433272222 | 1.487966667 |
| 1000-20 | 0.851887222 | 0.733853333 |

TABLE 2-continued

|  | Mr. A | Mr. B |
|---|---|---|
| 1000-10 | 5.698605556 | 6.154466667 |
| 1000-15 | 1.524722222 | 1.577183333 |
| 1000-20 | 0.834100556 | 0.721841111 |
| 1000-10 | 6.4488 | 3.088044444 |
| 1000-15 | 1.531481667 | 0.980582222 |
| 1000-20 | 0.902910556 | 0.57946 |
| 1000-10 | 7.364933333 | 5.939216667 |
| 1000-15 | 1.623872222 | 1.714438889 |
| 1000-20 | 0.890553333 | 0.804037222 |
| 1000-10 | 6.110144444 | 4.501644444 |
| 1000-15 | 1.487872222 | 1.397794444 |
| 1000-20 | 0.796442778 | 0.780930556 |
| 1000-10 | 4.772127778 | 6.441994444 |
| 1000-15 | 1.439755556 | 1.757077778 |
| 1000-20 | 0.756760556 | 0.780015 |
| 850-10 | 3.45905 | 5.327016667 |
| 850-15 | 1.467238889 | 2.070505556 |
| 850-20 | 0.987551111 | 1.107289444 |
| 850-10 | 7.561305556 | 10.25146667 |
| 850-15 | 2.239427778 | 2.566361111 |
| 850-20 | 1.224383333 | 1.388966667 |
| 850-10 | 6.226705556 | 11.22901667 |
| 850-15 | 2.154222222 | 3.473455556 |
| 850-20 | 1.152697222 | 1.470022222 |
| 850-10 | 5.645027778 | 9.872733333 |
| 850-15 | 2.273744444 | 2.293561111 |
| 850-20 | 1.424894444 | 1.0405 |
| 850-10 | 7.380116667 | 10.22521111 |
| 850-15 | 1.729977778 | 3.073222222 |
| 850-20 | 1.178283333 | 1.519083333 |
| 850-10 | 6.545427778 | 7.215466667 |
| 850-15 | 1.764261111 | 2.151677778 |
| 850-20 | 1.045702222 | 0.890543889 |
| 850-10 | 9.715116667 | 6.107811111 |
| 850-15 | 2.696177778 | 1.827844444 |
| 850-20 | 1.589238889 | 0.892885 |
| 850-10 | 11.26791111 | 9.704455556 |
| 850-15 | 3.24985 | 3.335122222 |
| 850-20 | 1.788977778 | 1.3699 |
| 850-10 | 8.316322222 | 9.210383333 |
| 850-15 | 2.831155556 | 2.889338889 |
| 850-20 | 1.452088889 | 1.520305556 |
| 850-10 | 7.499888889 | 7.865677778 |
| 850-15 | 2.441416667 | 2.601811111 |
| 850-20 | 1.339133333 | 1.104042222 |
| 809-10 | 3.170061111 | 4.689722222 |
| 809-15 | 1.319861111 | 1.78615 |
| 809-20 | 0.894047778 | 0.952103333 |
| 809-10 | 7.225544444 | 8.394538889 |
| 809-15 | 1.973377778 | 2.263955556 |
| 809-20 | 1.04445 | 1.200763333 |
| 809-10 | 5.965661111 | 8.082483333 |
| 809-15 | 2.08035 | 2.573683333 |
| 809-20 | 1.066636667 | 1.258983333 |
| 809-10 | 5.4605 | 6.525366667 |
| 809-15 | 1.933588889 | 1.7517 |
| 809-20 | 1.126208889 | 0.850663889 |
| 809-10 | 5.2216 | 6.195788889 |
| 809-15 | 1.187690556 | 2.040483333 |
| 809-20 | 0.925057222 | 1.057282778 |
| 809-10 | 4.733644444 | 5.119066667 |
| 809-15 | 1.530066667 | 1.526533333 |
| 809-20 | 0.855440556 | 0.600831111 |
| 809-10 | 8.724938889 | 4.444033333 |
| 809-15 | 2.772738889 | 1.64705 |
| 809-20 | 1.42645 | 0.751515 |
| 809-10 | 8.4446 | 8.504933333 |
| 809-15 | 2.655322222 | 2.908788889 |
| 809-20 | 1.545044444 | 1.327483333 |
| 809-10 | 7.226483333 | 7.986933333 |
| 809-15 | 2.362955556 | 2.579811111 |
| 809-20 | 1.147774444 | 1.287155556 |
| 809-10 | 6.984855556 | 6.944061111 |
| 809-15 | 2.280483333 | 2.083372222 |
| 809-20 | 1.225744444 | 0.983845 |
| 800-10 | 2.910116667 | 8.33995 |
| 800-15 | 1.359416667 | 2.426427778 |
| 800-20 | 0.877841111 | 1.099363889 |

TABLE 2-continued

| | Mr. A | Mr. B |
|---|---|---|
| 800-10 | 6.798494444 | 7.205988889 |
| 800-15 | 2.5559 | 2.072422222 |
| 800-20 | 1.132556111 | 1.554005556 |
| 800-10 | 5.713427778 | 7.471527778 |
| 800-15 | 1.994883333 | 2.562666667 |
| 800-20 | 0.986567222 | 1.162256111 |
| 800-10 | 5.032677778 | 6.597688889 |
| 800-15 | 1.767094444 | 1.572305556 |
| 800-20 | 1.03858 | 0.817647222 |
| 800-10 | 4.327433333 | 4.881333333 |
| 800-15 | 1.067463889 | 2.108938889 |
| 800-20 | 0.912270556 | 0.970358333 |
| 800-10 | 3.399727778 | 4.502477778 |
| 800-15 | 1.483372222 | 1.229805556 |
| 800-20 | 0.787231111 | 0.584085556 |
| 800-10 | 8.351344444 | 4.622316667 |
| 800-15 | 2.439794444 | 1.431733333 |
| 800-20 | 1.3061 | 0.676764444 |
| 800-10 | 7.797511111 | 10.89373889 |
| 800-15 | 2.701322222 | 3.542333333 |
| 800-20 | 1.54585 | 1.395666667 |
| 800-10 | 6.502966667 | 8.190383333 |
| 800-15 | 1.979872222 | 2.701938889 |
| 800-20 | 1.155616667 | 1.393477778 |
| 800-10 | 6.381516667 | 6.44475 |
| 800-15 | 2.301 | 1.737683333 |
| 800-20 | 1.153988889 | 0.911927778 |

In Table 2, for example, "1000-10" of the left column represents a condition of a wavelength of 1000 mm and an irradiation-detection distance of 10 mm, and light intensities (voltages mV detected with a photodiode) at respective detection positions of Mr. A and Mr. B under respective conditions are shown.

Figure 20:
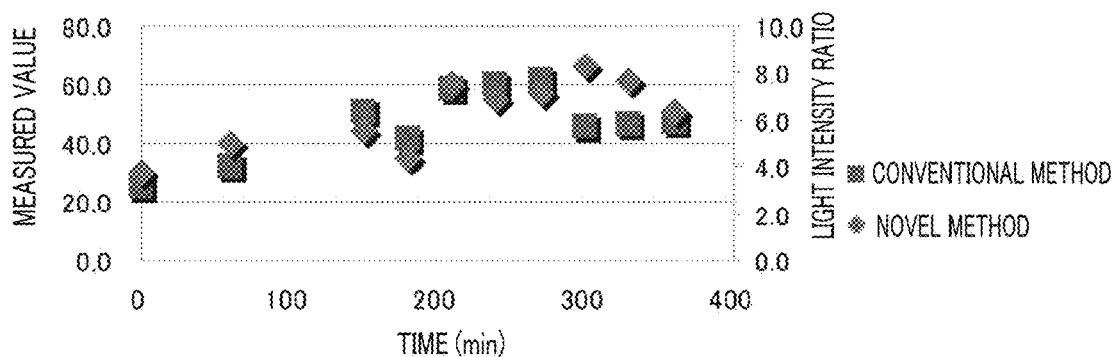
FIG. 20 is a graph showing ratios of light intensities detected at detection positions of Mr. A in Example 5.
Figure 21:
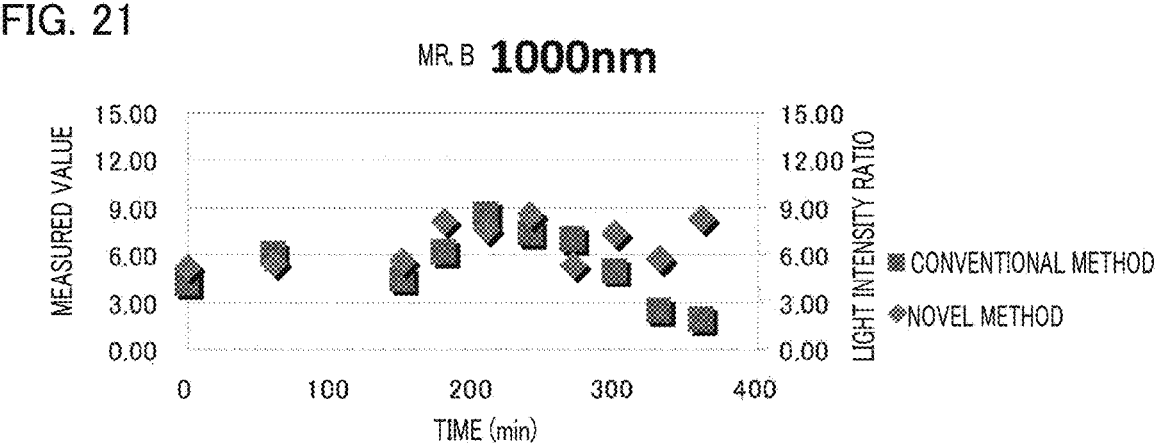
FIG. 21 is a graph showing ratios of light intensities detected at detection positions of Mr. B in Example 5.

(2) Calculation of Scattering Coefficient $\mu_s'$ Based on Ratio of Light Intensity Subsequently, the ratio of light intensities detected at detection positions 33 was calculated, and the ratio thus calculated was used as scattering coefficient $\mu_s'$. The value of the scattering coefficient $\mu_s'$ thus obtained is an index that represents scattering of emitted light by blood lipid. FIG. 20 and FIG. 21 are graphs showing values of scattering coefficients $\mu_s'$. In FIG. 20 and FIG. 21, the abscissa represents the time elapsed from the examinee's ingestion of lipid, and the ordinate represents the TG concentration in CM/VLDL measured with use of a conventional HPLC method, and scattering coefficient $\mu_s'$ obtained from the ratio of the light intensities detected at detection positions 33.

As shown in FIG. 20 and FIG. 21, the shapes of the graph of the values of scattering coefficient $\mu_s'$ and the graph of triglyceride (TG) concentration in CM/VLDL measured by the conventional HPLC method were similar to each other.

Figure 22:
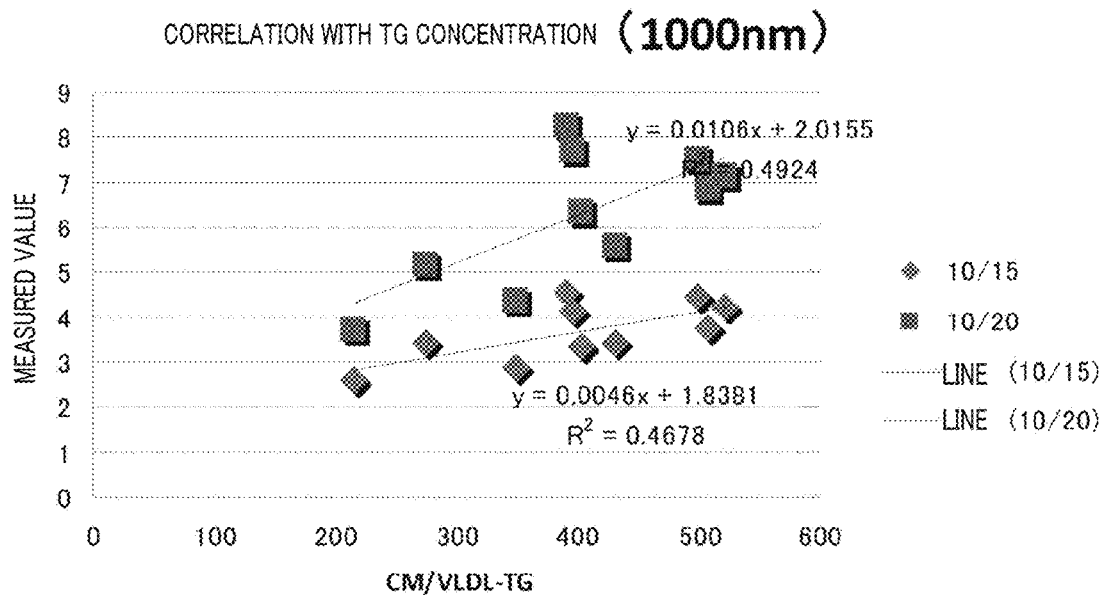
FIG. 22 is a graph a value of a ratio of light intensities detected at detection positions versus a TG concentration in CM/VLDL measured by a conventional HPLC method in Example 5.

In addition, FIG. 22 was prepared with the abscissa representing the values of scattering coefficient $\mu_s'$, and the ordinate representing triglyceride (TG) concentration in CM/VLDL measured with use of HPLC. Here, the diamond-shaped plot represents the ratio of the light intensity at a detection position distanced by 10 mm from irradiation position 21 to the light intensity at a detection position distanced by 15 mm from irradiation position 21, and the quadrangular plot represents the ratio of the light intensity at a detection position distanced by 10 mm from irradiation position 21 to the light intensity at a detection position distanced by 20 mm from irradiation position 21.

As shown in FIG. 22, it was confirmed that the values of scattering coefficient $\mu_s'$ and the triglyceride (TG) concentration in CM/VLDL measured with use of HPLC have a correlation with each other. Specifically, it was confirmed that the greater the detected light intensity, the greater the triglyceride (TG) concentration since the greater the value of scattering coefficient $\mu_s'$, the greater the triglyceride (TG) concentration. These results clearly show that the blood lipid concentration can be measured without blood collection by emitting light from the outside of a living body and calculating the influence of scattering by blood lipid from the detected light intensity.

In addition, when the variation in triglyceride concentration can be continuously measured in a time dependent manner in this manner, non-invasive lipid metabolism measurement, which has been conventionally difficult, is achieved, and consequently evaluation of the lever function as well as arteriosclerosis are expected to be achieved.

Figure 23:
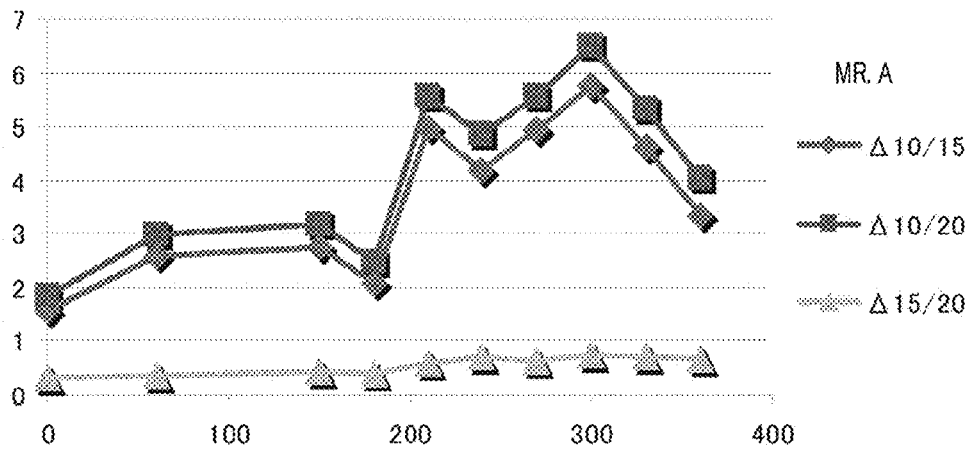
FIG. 23 is a graph showing differences of light intensities detected at detection positions of Mr. A in Example 5.
Figure 24:
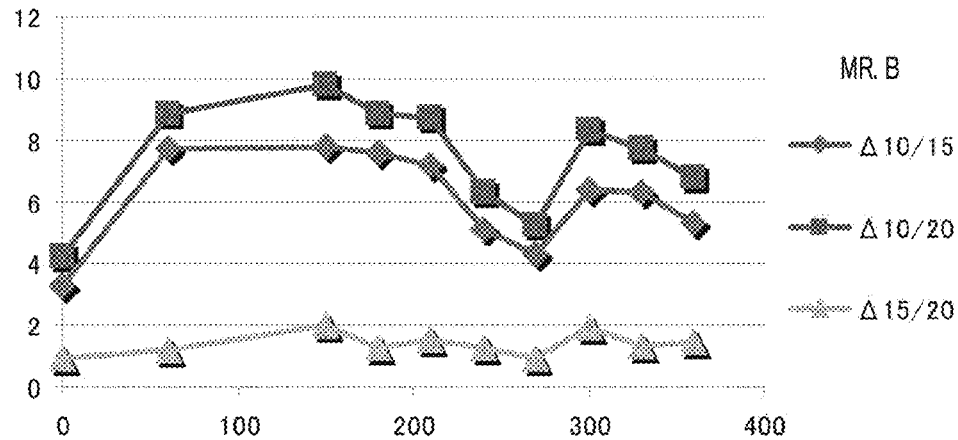
FIG. 24 is a graph showing differences of light intensities detected at detection positions of Mr. B in Example 5.

(3) Calculation of Scattering Coefficient $\mu_s'$ Based on Difference in Light Intensity In addition, the difference of light intensities detected at detection positions 33 were calculated, and the calculated difference was used as scattering coefficient $\mu_s'$. FIG. 23 and FIG. 24 are graphs showing values of scattering coefficient $\mu_s'$. In FIG. 23 and FIG. 24, the abscissa represents the time elapsed from the examinee's ingestion of lipid, and the ordinate represents scattering coefficient $\mu_s'$ obtained from the difference of the light intensities detected at detection positions 31. In addition, the diamond-shaped plot represents the difference between the light intensity at a detection position distanced by 10 mm from irradiation position 21 and the light intensity at a detection position distanced by 15 mm from irradiation position 21, the quadrangular plot represents the difference between the light intensity at a detection position distanced by 10 mm from irradiation position 21 and the light intensity at a detection position distanced by 20 mm from irradiation position 21, and the triangular plot represents the difference between the light intensity at a detection position distanced by 15 mm from irradiation position 21 and the light intensity at a detection position distanced by 20 mm from irradiation position 21.

Comparing FIGS. 23 and 24 and FIGS. 8 and 9, the shapes of the graphs (FIG. 23 and FIG. 24) of the values of the difference and the shape of the graphs (FIG. 8 and FIG. 9) of the triglyceride (TG) concentration in CM/VLDL measured by the conventional HPLC method were similar to each other. Specifically, it was confirmed that the greater the detected light intensity, the greater the triglyceride (TG) concentration since the greater the value of the difference, the greater the triglyceride (TG) concentration. These results clearly show that the blood lipid concentration can be measured without blood collection by emitting light from the outside of a living body and calculating the influence of scattering by blood lipid from the detected light intensity.

<Example 6> Studies on Expression (1) and Expression (2) by Simulation and Experiment In Example 6, an experiment using a biological tissue simulated phantom and ideal scattering phenomenon were calculated using Monte Carlo simulation, and with use of the value thus obtained, the following Expression (1) and Expression (2) were studied.

$$\ln\left\{\rho^2 \frac{R(\rho)}{S_0}\right\} = -\mu_{eff}\rho + \ln\frac{3\mu_a}{2\pi\mu_{eff}} \quad \text{[Expression 1]}$$

$$\ln\left\{\rho^3 \frac{R(\rho)}{S_0}\right\} = -\mu_{eff}\rho + \ln\frac{1}{2\pi\mu_s'} \quad \text{[Expression 2]}$$

(1) Studies on Expression (1) and Expression (2) by Monte Carlo Simulation

Figure 25:
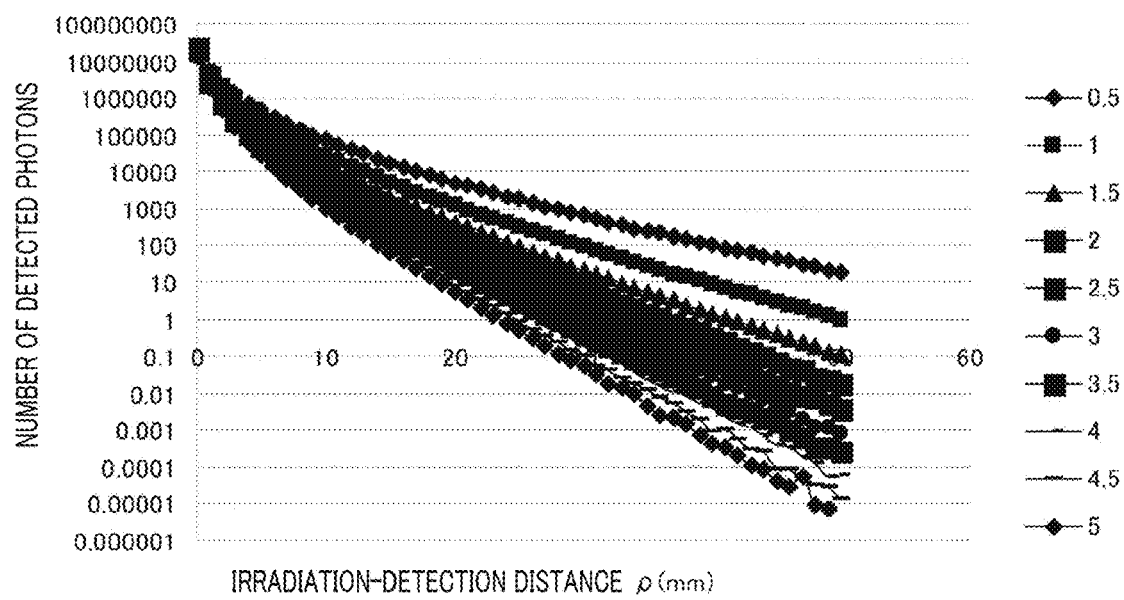
FIG. 25 is a graph showing results of a Monte Carlo simulation of irradiation-detection distance $\rho$ and the number of detected photons in Example 6.

First, by Monte Carlo simulation, irradiation-detection distance ρ and number of detected photons were simulated. The condition of this simulation is the absorption coefficient of 0.01, and the number of emitted photons of $10\times10^9$. The calculation was performed with scattering coefficients $\mu_s'$ of 0.5, 1, 1.5, 2, 2.5, 3, 3.5, 4, 4.5 and 5. FIG. shows results of the calculation. In FIG. 25, the abscissa represents irradiation-detection distance ρ, and the ordinate represents the number of detected photons.

As shown in FIG. 25, as irradiation-detection distance ρ is increased, the number of detected photons is reduced by scattering.

Figure 26:
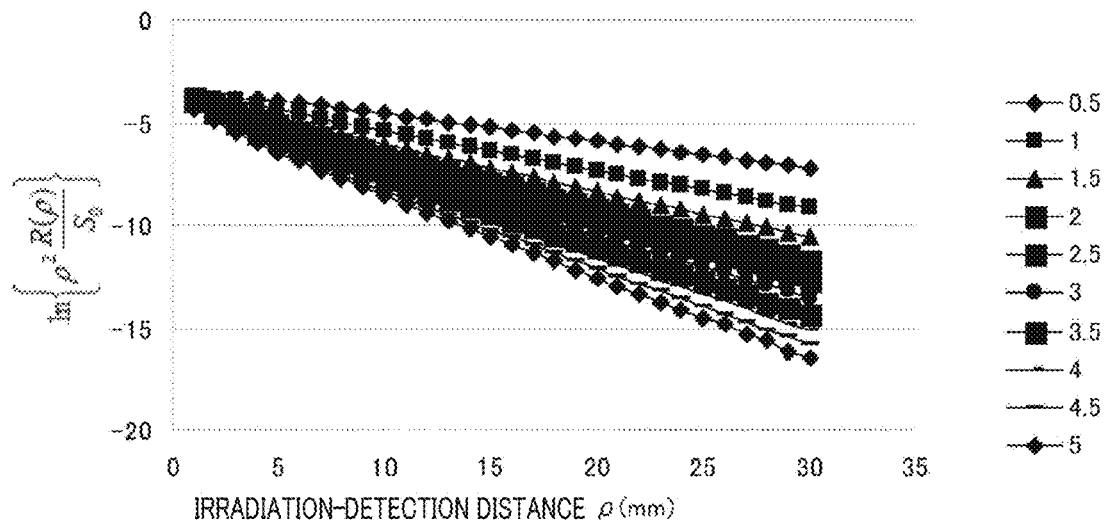
FIG. 26 is a graph showing results obtained by applying results of the Monte Carlo simulation into Expression (1) in Example 6.

Next, the results of the Monte Carlo simulation were applied into Expression (1). Results are shown in FIG. 26. In FIG. 26, the abscissa represents irradiation-detection distance ρ, and the ordinate represents the degree of attenuation of light with respect to the incident light, which is the incident light attenuation rate in Example 6.

Here, since it is speculated that the irradiation-detection distance in actual measurement is required to be equal to or greater than 1 cm, the calculation range of the gradients and the intercepts were set to 1 cm to 3 cm. At this time, from Expression (1), the gradients of these values correspond to effective attenuation coefficient $\mu_{eff}$, and the intercepts correspond to $\ln(3\mu_a/2\pi\mu_{eff})$ of the following Expression (16).

$$\ln\left\{\rho^2 \frac{R(\rho)}{S_0}\right\} = -\mu_{eff}\rho + \ln\frac{3\mu_a}{2\pi\mu_{eff}} \quad \text{[Expression 16]}$$

Figure 27:
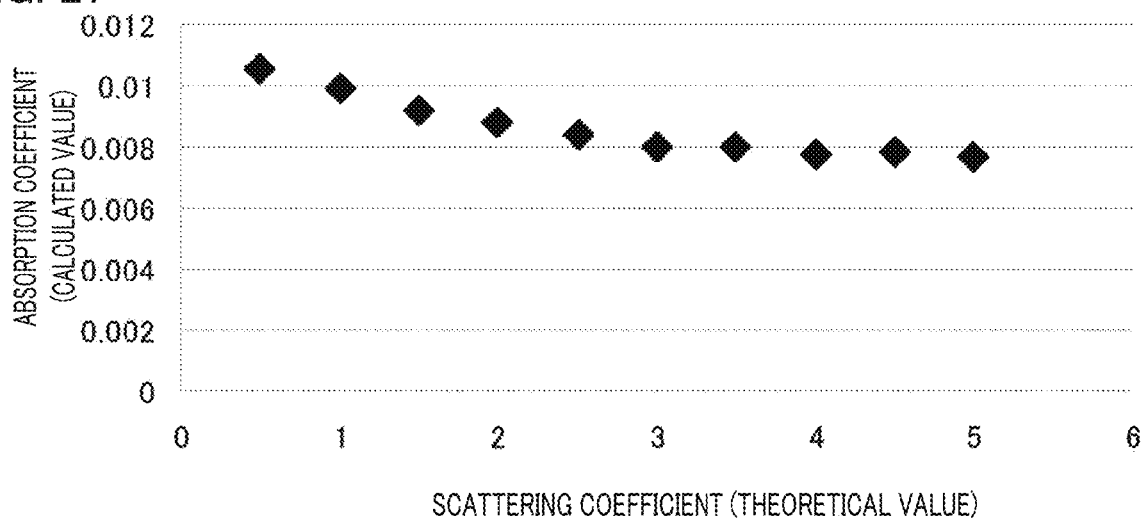
FIG. 27 is a graph showing absorption coefficient $\mu_a$ obtained from intercepts of the graph of FIG. 26.

That is, absorption coefficient $\mu_a$ can be determined from the intercepts of the graph of the incident light attenuation rate shown in FIG. 26. FIG. 27 shows absorption coefficients $\mu_a$ thus determined. In FIG. 27, the abscissa represents scattering coefficient $\mu_s'$, and the ordinate represents absorption coefficient $\mu_a$ determined from the intercepts. As shown in FIG. 27, absorption coefficient $\mu_a$ was gradually changed toward 0.008 with respect to the theoretical value of 0.01 of the calculation condition, which is numerically approximated value.

Further, the effective attenuation coefficient $\mu_{eff}$ was calculated from the gradients of the graph of the incident light attenuation rate shown in FIG. 26, and scattering coefficient $\mu_s'$ was calculated from the following Expression (8).

$$\mu_{eff} \approx \sqrt{3\mu_a \mu_s'} \quad \text{[Expression 8]}$$

Figure 28:
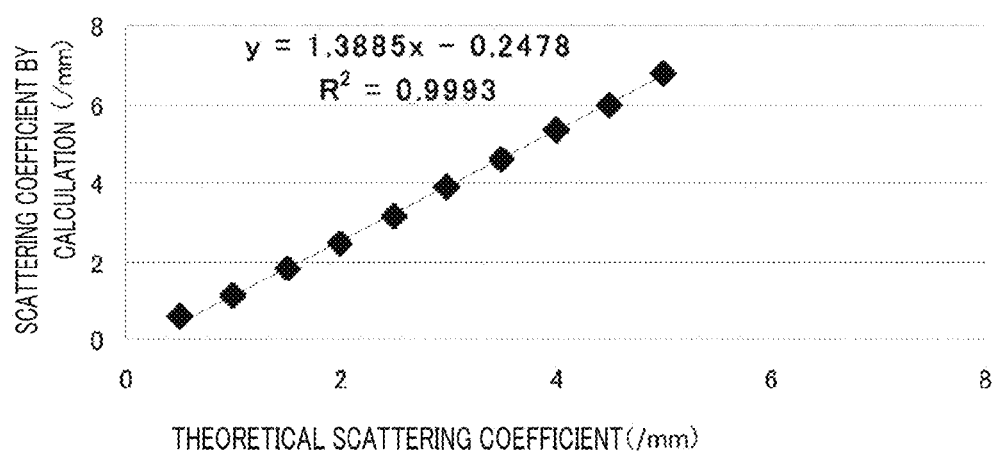
FIG. 28 is a graph of theoretical scattering coefficient $\mu_s'$ versus scattering coefficient $\mu_s'$ calculated by applying into Expression (8) effective attenuation coefficient $\mu_{eff}$ calculated from gradients of the graph of FIG. 26.

Results are shown in FIG. 28. In FIG. 28, the abscissa represents the theoretical value used as the calculation condition, and the ordinate represents the value calculated based on Expression (8).

As shown in FIG. 28, the theoretical values and the calculation values are sufficiently agree with each other, and in linear approximation of the theoretical values and the calculation values, the correlation function of agreement of 0.99 or higher was obtained.

Figure 29:
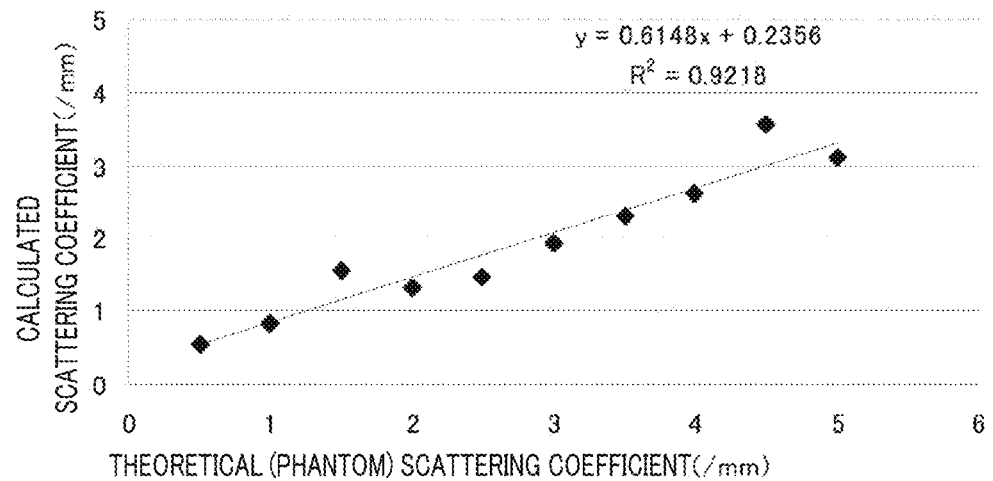
FIG. 29 is a graph of simulated phantom scattering coefficient $\mu_s'$ versus results obtained by calculating simulated phantom scattering coefficient $\mu_s'$ using Expression (1) and Expression (3) by experiment in Example 6.

(2) Studies on Expression (1) and Expression (2) by Experiment Based on Biological Tissue Simulated Phantom Next, an experiment was performed based on a biological tissue simulated phantom having a specific scattering coefficient $\mu_s'$ which was prepared using Intralipid. To be more specific, biological tissue simulated phantoms having scattering coefficients $\mu_s'$ of 0.5, 1, 1.5, 2, 2.5, 3, 3.5, 4, 4.5 and 5 were prepared. The biological tissue simulated phantoms were irradiated with consecutive light by irradiator 2, and the light intensity was detected by light intensity detector 4. As with Example (1), the light intensity thus detected was applied into Expression (1) and Expression (2) to calculate scattering coefficient $\mu_s'$. Results are shown in FIG. 29. In FIG. 29, the abscissa represents scattering coefficient $\mu_s'$ of the biological tissue simulated phantom, and the ordinate represents scattering coefficient $\mu_s'$ calculated by applying detected light intensity into Expression (1) and Expression (2).

As shown in FIG. 29, also in the experiment, theoretical values and calculation values are sufficiently agree with each other, and in linear approximation of the theoretical values and the calculation values, agreement of 0.92 or higher of the correlation function was obtained. Thus, also in the experiment, measurement was achieved with very high accuracy.

The above-mentioned results show that scattering coefficient $\mu_s'$ can be measured with use of Expression (1) and Expression (2) even when absorption coefficient $\mu_a$ is unknown. In addition, it was confirmed that, as can be seen in the correlation coefficient, the scattering coefficient can be calculated with higher accuracy by measurement at multiple points even with a large amount of noise in actual measurement of a living body.

<Example 7> Studies on Expression (3) by Simulation and Experiment

In Example 7, the following Expression (3) was studied by an experiment using a biological tissue simulated phantom and calculation of an ideal scattering phenomenon using Monte Carlo simulation.

$$\mu_s' = \frac{1}{3\mu_a}\left\{\frac{1}{\rho_2 - \rho_1}\ln\frac{\rho_1^2 R(\rho_1)}{\rho_2^2 R(\rho_2)}\right\}^2 \quad \text{[Expression 3]}$$

(1) Studies on Irradiation-Detection Distance

From Expression (3), the sensitivity of scattering coefficient $\mu_s'$ is enhanced as the ratio of light intensity R ($\rho_1$) to light intensity R ($\rho_2$) at the first detection position is increased. Therefore, the greater the distance between $\rho_1$ and $\rho_2$, the more preferable. However, light intensity R (ρ) exponentially decreases as irradiation-detection distance ρ increases, and S/N ratio, which is the ratio of the signal quantity (signal) to the noise quantity (noise), in measurement are quickly increased, thus degrading the measurement accuracy. In addition, when the difference in distance between $\rho_1$ and $\rho_2$ is increased, common part of internal scattering member propagation region of light intensity of the points is reduced, thus further degrading the measurement accuracy. Given the above, the measurement condition was studied to determine favorable measurement conditions by changing $\rho_1$ and $\rho_2$ in a range of practical use.

Figure 30:
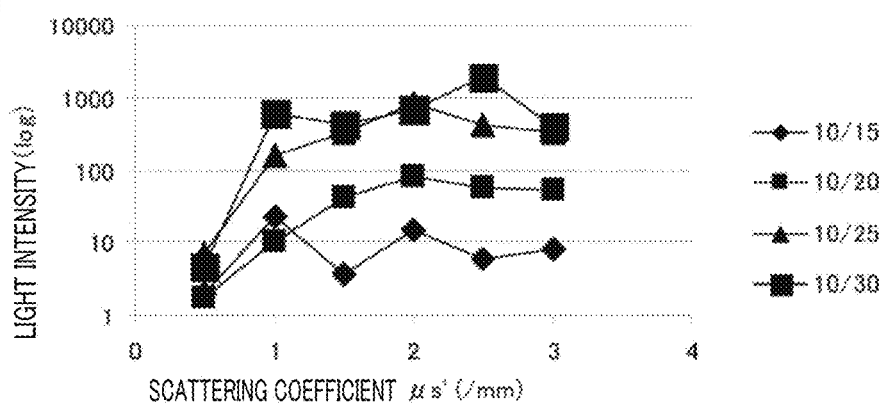
FIG. 30 is a graph of scattering coefficient $\mu_s'$ versus measured variations of a ratio of light intensity R ($\rho_1$)/R ($\rho_2$) in Example 7.

(2) Studies on Irradiation-Detection Distance ρ by Biological Tissue Simulated Phantom First, a biological tissue simulated phantom having a specific scattering coefficient $\mu_s'$ was prepared using Intralipid. In this experiment, with use of Intralipid, variation of R ($\rho_1$)/R ($\rho_2$) with respect to scattering coefficient $\mu_s'$ was measured. Exemplary measurement results are shown in FIG. 30. In FIG. 30, the abscissa represents the scattering coefficient, and the ordinate represents the light intensity. In addition, the diamond-shaped plot represents the ratio of the light intensity at a detection position distanced by 10 mm from irradiation position 21 to the light intensity at a detection position distanced by 15 mm from irradiation position 21, the quadrangular plot represents the ratio of the light intensity at a detection position distanced by 10 mm from irradiation position 21 to the light intensity at a detection position distanced by 20 mm from irradiation position 21, the triangular plot represents the ratio of the light intensity at a detection position distanced by 10 mm from irradiation position 21 to the light intensity at a detection position distanced by 25 mm from irradiation position 21, and the cross-shaped plot represents the ratio of the light intensity at a detection position distanced by 10 mm from irradiation position 21 to the light intensity at a detection position distanced by 30 mm from irradiation position 21.

Here, a calibration curve for estimating $\mu_s'$ from measurement results of $(\rho_1)/R(\rho_2)$ is desirably a stable simple variation. From this view point, in FIG. 30, the case of $\rho_1=10$ mm and $\rho_2=20$ mm was most favorable. Through such an analysis, in the subsequent experiment using the biological tissue simulated phantom and a simulation by Monte Carlo simulation, an experiment was performed with detection positions set to $\rho_1=10$ mm and $\rho_2=20$ mm.

(3) Studies on Expression (3) by Monte Carlo Simulation

Figure 31:
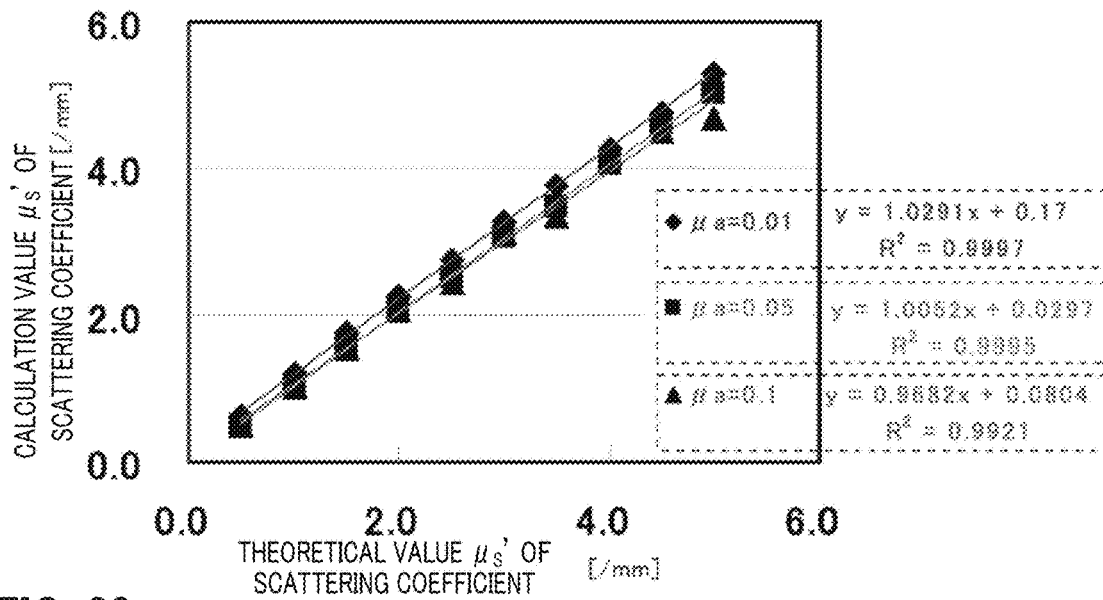
FIG. 31 is a graph of theoretical scattering coefficient $\mu_s'$ versus scattering coefficient $\mu_s'$ calculated using Expression (3) in Example 7.

To verify the adequacy of Expression (3), verification was performed by Monte Carlo simulation. The condition of simulation was absorption coefficient $\mu_a$ of 0.01, 0.05 and 0.1. Scattering coefficient $\mu_s'$ was set to 0.5, 1, 1.5, 2, 2.5, 3, 3.5 and 4 and calculation was performed for each combination. In addition, irradiation-detection distance $\rho$ was set to $\rho_1=10$ mm and $\rho_2=20$ mm as described above. Then, the value thus obtained was applied into Expression (3), and calculation was performed. Results of the calculation are shown in FIG. 31. In FIG. 31, the abscissa represents theoretical scattering coefficient $\mu_s'$ that serves also as the simulation condition, and the ordinate represents scattering coefficient $\mu_s'$ calculated using Expression (3).

As shown in FIG. 31, theoretical scattering coefficient $\mu_s'$ and scattering coefficient $\mu_s'$ calculated using Expression (3) are sufficiently agree with each other, and in linear approximation of the theoretical value and the calculation value, the gradients fell within an error range of about 1 to 3%, and the correlation function of 0.99 or higher was consistently satisfied.

Figure 32:
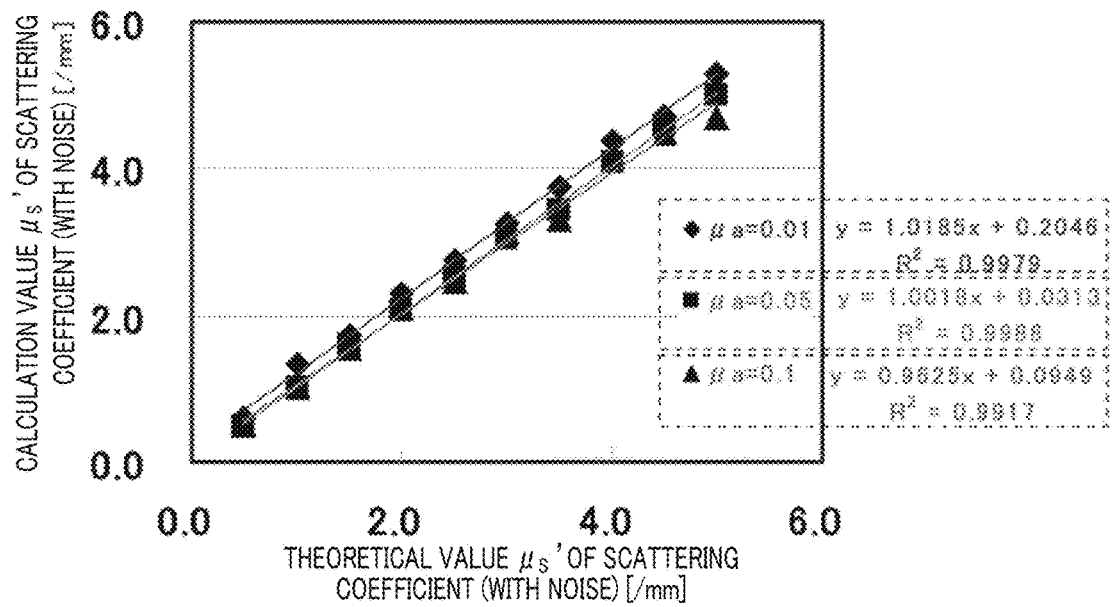
FIG. 32 is a graph of theoretical scattering coefficient $\mu_s'$ obtained by adding noise of 5% to the detected light intensity, versus scattering coefficient $\mu_s'$ calculated using Expression (3) in Example 7.

Likewise, theoretical scattering coefficient $\mu_s'$ and scattering coefficient $\mu_s'$ calculated using Expression (3) in the case where noise (±5%) is added to the detected light intensity were also studied. Results of the calculation are shown in FIG. 32. In FIG. 32, the abscissa represents theoretical scattering coefficient $\mu_s'$ that serves also as the simulation condition, and the ordinate represents scattering coefficient $\mu_s'$ calculated using Expression (3).

As shown in FIG. 32, even in the case where noise is added, the theoretical value and the calculation value were sufficiently agree with each other.

(4) Studies on Expression (3) by Experiment Based on Biological Tissue Simulated Phantom Given the results of Monte Carlo simulation, Expression (3) was studied by an experiment using a biological tissue simulated phantom. Results of measurement are shown in FIG. 32. The abscissa represents scattering coefficient $\mu_s'$ of the biological tissue simulated phantom, and the ordinate represents scattering coefficient $\mu_s'$ calculated by calculating the light intensity by the experiment and then applying the calculated light intensity into Expression (3).

Figure 33:
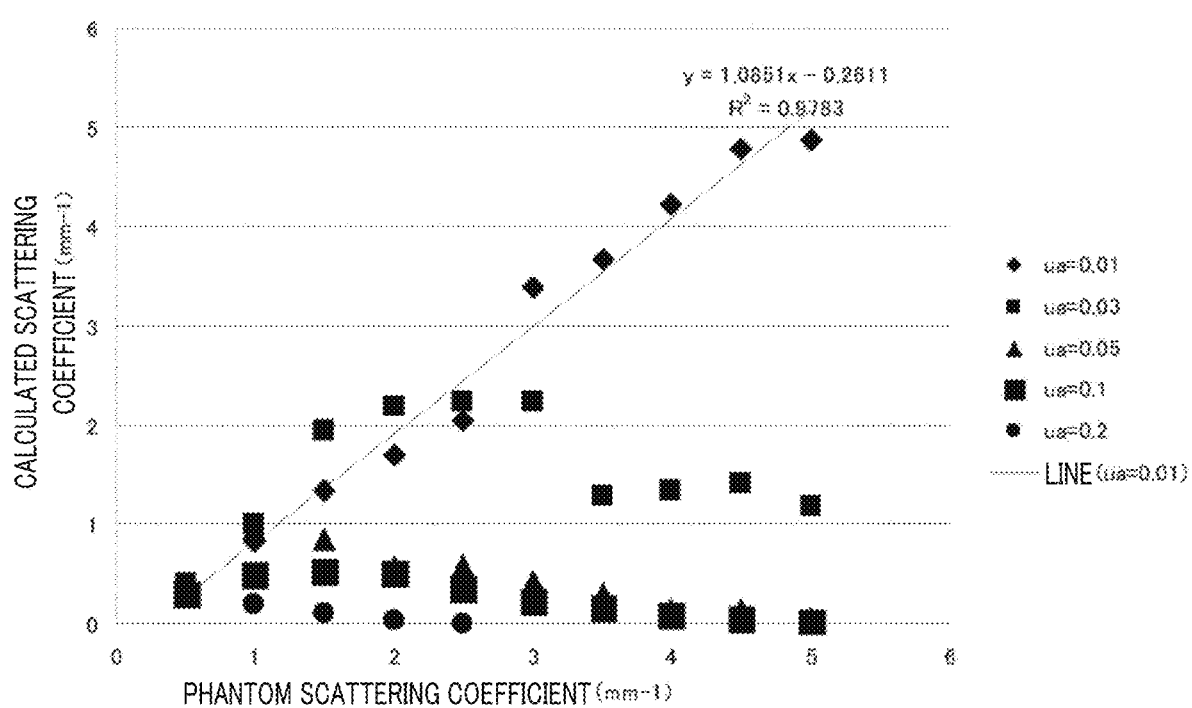
FIG. 33 is a graph of simulated phantom scattering coefficient $\mu_s'$ versus simulated phantom scattering coefficient $\mu_s'$ calculated using Expression (3) by experiment in Example 7.

As shown in FIG. 33, the greater the absorption coefficient, the lower the accuracy. However, absorption coefficient $\mu_a$ of a typical living body is about 0.01/mm, and in the absorption coefficient $\mu_a$ in this case, scattering coefficient $\mu_s'$ of the biological tissue simulated phantom and scattering coefficient $\mu_s'$ calculated using Expression (3) are sufficiently agree with each other. In linear approximation of the scattering coefficient $\mu_s'$ of the biological tissue simulated phantom and the calculation value, the correlation function of 0.97 was satisfied.

Thus, it was confirmed that scattering coefficient $\mu_s'$ can be calculated with use of Expression (3) under a condition of a typical living body.

It is to be noted that the non-invasive biolipid concentration measuring device, the non-invasive biolipid metabolism measuring device, the method of non-invasively measuring biolipid concentration and the method of non-invasively examining biolipid metabolism according to the embodiment of the present invention are not limited to the above-described embodiment, and may be appropriately changed.

For example, it is possible to cover irradiator 2 and light intensity detector 3 with a light-shielding cover, or to perform measurement in a dark place, in order to block other light than emitted light and received light.

In addition, while non-invasive measurement with respect to a living body has been described in the present embodiment, the present embodiment is also applicable to non-invasive measurement with respect to a test tube or the like for blood test and serum test in the test tube or the like. In this case, the present embodiment is applicable to turbidity measurement or the like in serum information (hemolysis, high bilirubin, milky fluid and the like) prior to a blood test.

REFERENCE SIGNS LIST

1 Non-invasive biolipid concentration measuring device
2 Irradiator
3 Light intensity detector
4 Scattering coefficient calculator
5 Lipid concentration calculator
10 Non-invasive biolipid metabolism measuring device
21 Irradiation position
22 Light source
31 First light intensity detector
32 Second light intensity detector
33 Detection position
331 First detection position
332 Second detection position
41 Light intensity/distance calculation unit
42 Light intensity ratio calculation unit
43 Light intensity difference calculation unit
44 Attenuation time calculation unit
45 Highest intensity time calculation unit
46 Light-density waveform calculation unit
101 Calculated-value acquirer
102 Biolipid metabolism determinator

The invention claimed is:
1. A non-invasive biolipid concentration measuring device configured to non-invasively measure a concentration of lipid in blood in a living body, the non-invasive biolipid concentration measuring device comprising:
an irradiator configured to emit light having wavelength being either 580 nm to 1400 nm or 1500 nm to 1860 nm toward an irradiation position of the living body;

a plurality of light intensity detectors disposed at respective detection positions differing in distance from the irradiation position, the plurality of light intensity detectors being configured to detect intensities of light emitted from the irradiator at the respective detection positions;

a scattering coefficient calculator configured to calculate a light scattering coefficient and an absorption coefficient of the living body based on light intensities detected by the plurality of light intensity detectors; and a lipid concentration calculator configured to calculate the concentration of the lipid in the blood based on the light scattering coefficient and the absorption coefficient calculated by the scattering coefficient calculator, wherein the lipid is a large lipoprotein selected from the group consisting of a chylomicron (CM) and a very-low-density lipoprotein (VLDL), and wherein the scattering coefficient calculator separates an effective attenuation coefficient obtained by a single detection with the plurality of light intensity detectors into the light scattering coefficient and the absorption coefficient which are unknown, and wherein the scattering coefficient calculator calculates the effective attenuation coefficient from the gradient of a line obtained by linearizing an incident light attenuation rate with respect to an irradiation-detection distance between the irradiation position and the detection position, calculates the absorption coefficient from an intercept of the line and the effective attenuation coefficient, and then calculates the light scattering coefficient from the absorption coefficient and the effective attenuation coefficient.

2. A method of non-invasively measuring a biolipid concentration in which a concentration of lipid in blood in a living body is non-invasively measured, the method comprising:

(a) emitting light having wavelength being either 580 nm to 1400 nm or 1500 nm to 1860 nm towards an irradiation position of the living body;

(b) detecting intensities of light by a single detection with a plurality of light intensity detectors disposed at respective detection positions differing in distance from the irradiation position;

(c) calculating a light scattering coefficient and an absorption coefficient of the living body by separating an effective attenuation coefficient obtained by the single detection with the plurality of light intensity detectors into the light scattering coefficient and the absorption coefficient which are unknown; and (d) calculating the concentration of the lipid in the blood based on the light scattering coefficient and the absorption coefficient, wherein the lipid is a large lipoprotein selected from the group consisting of a chylomicron (CM) and a very-low-density lipoprotein (VLDL), wherein step (c) includes calculating the effective attenuation coefficient from the gradient of a line obtained by linearizing an incident light attenuation rate with respect to an irradiation detection distance between the irradiation position and the detection position, calculating the absorption coefficient from an intercept of the line and the effective attenuation coefficient, and then calculating the light scattering coefficient from the absorption coefficient and the effective attenuation coefficient.

* * * * *